(12) United States Patent
Ito

(10) Patent No.: US 10,138,452 B2
(45) Date of Patent: Nov. 27, 2018

(54) OBJECT-HOLDING DEVICE

(71) Applicant: YAMAHA HATSUDOKI KABUSHIKI KAISHA, Iwata-shi, Shizuoka-ken (JP)

(72) Inventor: Saburo Ito, Shizuoka (JP)

(73) Assignee: YAMAHA HATSUDOKI KABUSHIKI KAISHA, Shizuoka-ken (JP)

( * ) Notice: Subject to any disclaimer, the term of this patent is extended or adjusted under 35 U.S.C. 154(b) by 44 days.

(21) Appl. No.: 15/323,892

(22) PCT Filed: Aug. 5, 2014

(86) PCT No.: PCT/JP2014/070632
§ 371 (c)(1),
(2) Date: Jan. 4, 2017

(87) PCT Pub. No.: WO2016/020988
PCT Pub. Date: Feb. 11, 2016

(65) Prior Publication Data
US 2017/0145362 A1    May 25, 2017

(51) Int. Cl.
*C12M 1/32* (2006.01)
*C12M 1/34* (2006.01)
*C12M 1/00* (2006.01)

(52) U.S. Cl.
CPC ............ *C12M 23/12* (2013.01); *C12M 23/34* (2013.01); *C12M 29/14* (2013.01); *C12M 41/40* (2013.01); *C12M 47/04* (2013.01)

(58) Field of Classification Search
CPC ...... C12M 29/04; C12M 23/12; C12M 47/04; C12M 23/34; C12M 29/14; C12M 41/40
See application file for complete search history.

(56) References Cited

U.S. PATENT DOCUMENTS

2006/0252044 A1    11/2006 Okumura et al.
2007/0264705 A1    11/2007 Dodgson
(Continued)

FOREIGN PATENT DOCUMENTS

EP    1 068 902 A2    1/2001
EP    2 692 853 A1    2/2014
(Continued)

OTHER PUBLICATIONS

The extended European search report issued by the European Patent Office on Jul. 17, 2017, which corresponds to EP14899498.1-1501 and is related to U.S. Appl. No. 15/323,892.

(Continued)

*Primary Examiner* — Gautam Prakash
(74) *Attorney, Agent, or Firm* — Studebaker & Brackett PC

(57) ABSTRACT

An object-holding device includes a container, a plate, and a dispersing mechanism. The container is configured to store a liquid, and includes an upper opening for charging an object into the stored liquid, and a bottom wall. The plate has an upper surface and a lower surface and is immersed into the liquid in a state in which the lower surface is spaced away from the bottom wall of the container, with this plate including: one or a plurality of holding portions arranged on the upper surface side and configured to carry the object; and a through hole passing through the holding portion from the upper surface to the lower surface. The dispersing mechanism is configured to form, in the through hole, a liquid flow which flows from the lower surface side toward the upper surface side to raise the object carried on the holding portion.

6 Claims, 19 Drawing Sheets

(56) References Cited

U.S. PATENT DOCUMENTS

| | | | |
|---|---|---|---|
| 2010/0233799 A1* | 9/2010 | Takayama et al. | ............... B01L 3/50273 435/305.2 |
| 2011/0236970 A1 | 9/2011 | Larsen et al. | |
| 2012/0322144 A1 | 12/2012 | Lam et al. | |
| 2014/0322747 A1 | 10/2014 | Ito | |
| 2014/0341680 A1 | 11/2014 | Ito | |

FOREIGN PATENT DOCUMENTS

| | | | |
|---|---|---|---|
| JP | 2005-148048 A | 6/2005 |
| JP | 2007-504816 A | 3/2007 |
| JP | 2007-225425 A | 9/2007 |
| JP | 2009-504161 A | 2/2009 |
| JP | 2009-072130 A | 4/2009 |
| WO | 2007/022026 A2 | 2/2007 |
| WO | 2013/093954 A1 | 6/2013 |
| WO | 2013/093961 A1 | 6/2013 |

OTHER PUBLICATIONS

Database WPI Week 200926, Thomson Scientific, London, GB, AN 2009-G95130, XP002771612.

International Search Report issued in PCT/JP2014/070632; dated Nov. 11, 2014.

Zhang et al.; Automated Batch Transfer of Zebrafish Embryos Using a Multi-Degrees-of-Freedom System; 2011 IEEE International Conference on Robotics and Automation; May 9-13, 2011; pp. 2554-2559; Shanghai, China.

An Office Action; "Notification of Reasons for Refusal" issued by the Japanese Patent Office on Jun. 6, 2017, which corresponds to Japanese Patent Application No. 2016-117567 and is related to U.S. Appl. No. 15/323,892; with English language translation.

An Office Action issued by the Chinese Patent Office on May 10, 2018, which corresponds to Chinese Patent Application 201480080206.8 and is related to U.S. Appl. No. 15/323,892; with English Summary.

\* cited by examiner

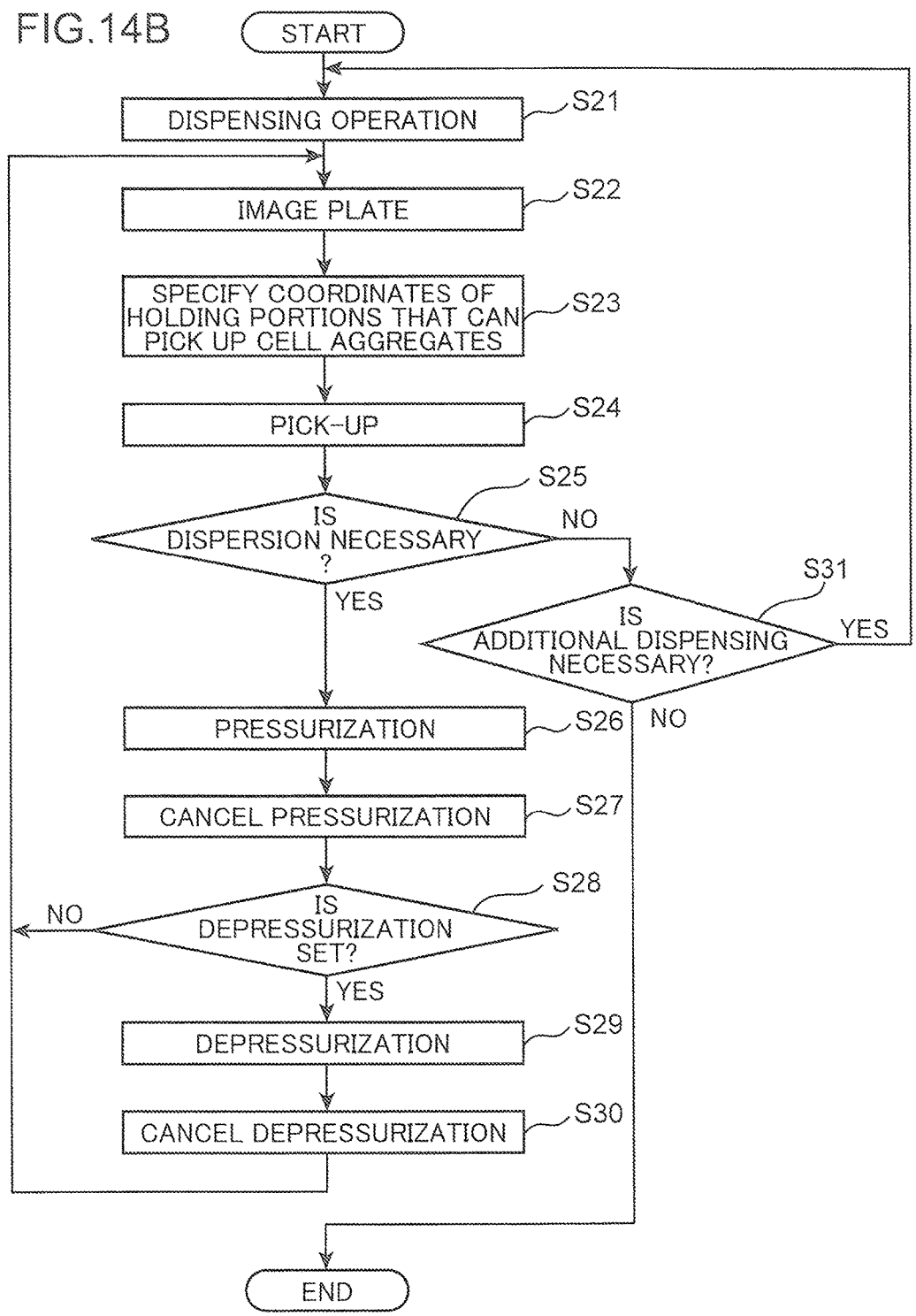

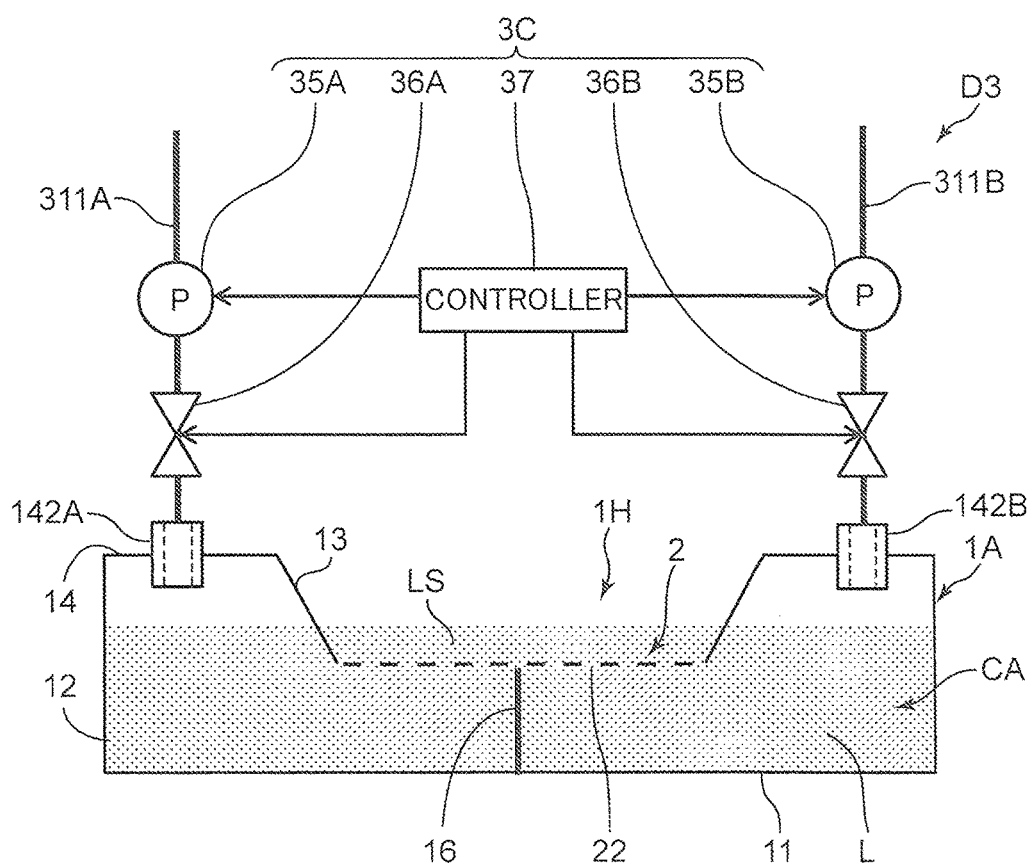

OBJECT-HOLDING DEVICE

CROSS REFERENCE TO RELATED APPLICATIONS

This application claims benefit of priority to International Patent Application No. PCT/JP2014/070632 filed Aug. 5, 2014, the entire content of which is incorporated herein by reference.

TECHNICAL FIELD

The present disclosure relates to a device configured to hold an object, such as a cell aggregate.

BACKGROUND

Devices configured to hold certain objects in a container that stores a liquid are required in some cases. For example, when the objects are cell aggregates, for the purpose of sorting, observation, cultivation, and the like of the cell aggregates, a plate including a large number of cell holding portions may be arranged in a cell culture liquid stored in the container, thereby holding the cell aggregates in the holding portions. Japanese Translation of PCT International Application publication No. 2009-504161 discloses a holding device configured to hold cells or beads for biological tests on a plate having a plurality of through holes formed as the cell aggregate holding portions.

In the holding device, it is generally desired that one cell aggregate be held in one holding portion. However, it is difficult to achieve such a desired holding state for cell aggregates. Specifically, when cell aggregates are to be held in the holding portions, a cell suspension containing a large number of cell aggregates is discharged from a dispenser tip into the cell culture liquid in the container. Positioning of the cell aggregates in the holding portions on the plate depends solely on natural precipitation that occurs after the discharge. Therefore, in many cases, the cell aggregates are carried on the plate in a state in which a plurality of cell aggregates are concentrated, or a large number of holding portions remain with no cell aggregates held therein.

As a measure to solve this problem, the plate is vibrated after the cell suspension is discharged. The vibration of the plate may raise such an expectation that the precipitated cell aggregates are dispersed. However, the holding device including a vibration device has a complicated structure. Further, when the holding portion has a shape of a recess and once the cell aggregates are caught in the recess, the cell aggregates cannot be released from the recess with a slight vibration. As a result, the effect of dispersing the cell aggregates may fail to meet the expected level.

SUMMARY

It is an object of the present disclosure to provide a holding device capable of holding an object in a satisfactorily dispersed state on a plate including a plurality of holding portions configured to carry the object.

An object-holding device according to one aspect of the present disclosure includes: a container configured to store a liquid, and having: an upper opening for charging an object into the stored liquid, and a bottom wall; a plate having an upper surface and a lower surface and immersed into the liquid in a state in which the lower surface is spaced away from the bottom wall of the container, with this plate including: one or a plurality of holding portions arranged on the upper surface side and configured to carry the object; and a through hole formed at a position, at which the holding portion is arranged, and passing through the holding portion from the upper surface to the lower surface; and a dispersing mechanism configured to form, in the through hole, a liquid flow which flows from the lower surface side toward the upper surface side to raise the object carried on the holding portion.

Objects, features and advantages of the present disclosure become more apparent from the following detailed description and the accompanying drawings.

BRIEF DESCRIPTION OF THE DRAWINGS

FIG. 14B is a flowchart illustrating another example of the control flow for the holding device, which is executed by the controller.

FIG. 17 is a block diagram schematically illustrating an object-holding device according to a third embodiment.

DETAILED DESCRIPTION

An object-holding device according to an embodiment of the present disclosure is now described in detail with reference to the accompanying drawings. In this embodiment, the case where an object is a biological cell, in particular, a cell aggregate, is described. The biological cell aggregate (spheroid) is formed by aggregating several to several hundred thousands of cells. Therefore, the cell aggregate varies in size. The cell aggregate formed by viable cells has a substantially spherical shape, but the shape of the cell aggregate may be distorted or the density thereof may be uneven when some of the cells forming the cell aggregate are altered or dead. In tests to be conducted in the fields of bio-related technology and medicine, the present disclosure is suitably applied to work of holding a plurality of cell aggregates having various shapes with the holding device of this embodiment to sort out only cell aggregates having shapes suited to the tests. Note that the object is not limited to a cell aggregate, and may be a compact electronic or mechanical part, an organic or inorganic fragment or particle, or a pellet.

Figure 1:
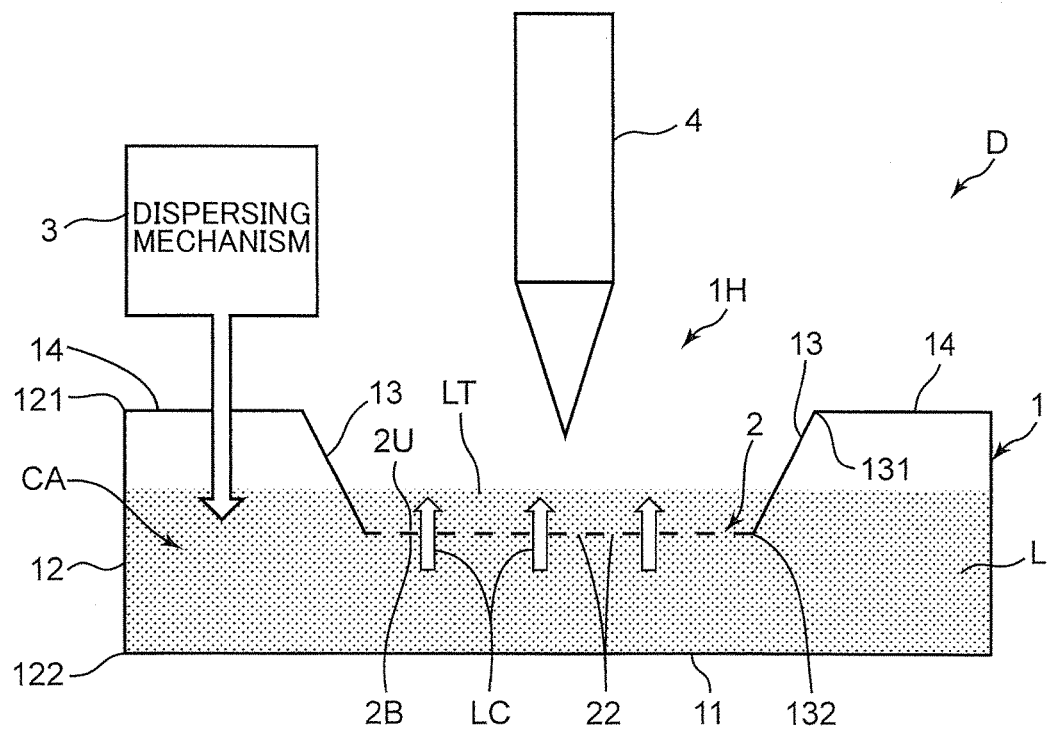
FIG. 1 is a side cross-sectional view schematically illustrating an object-holding device according to an embodiment of the present disclosure.
Figure 2:
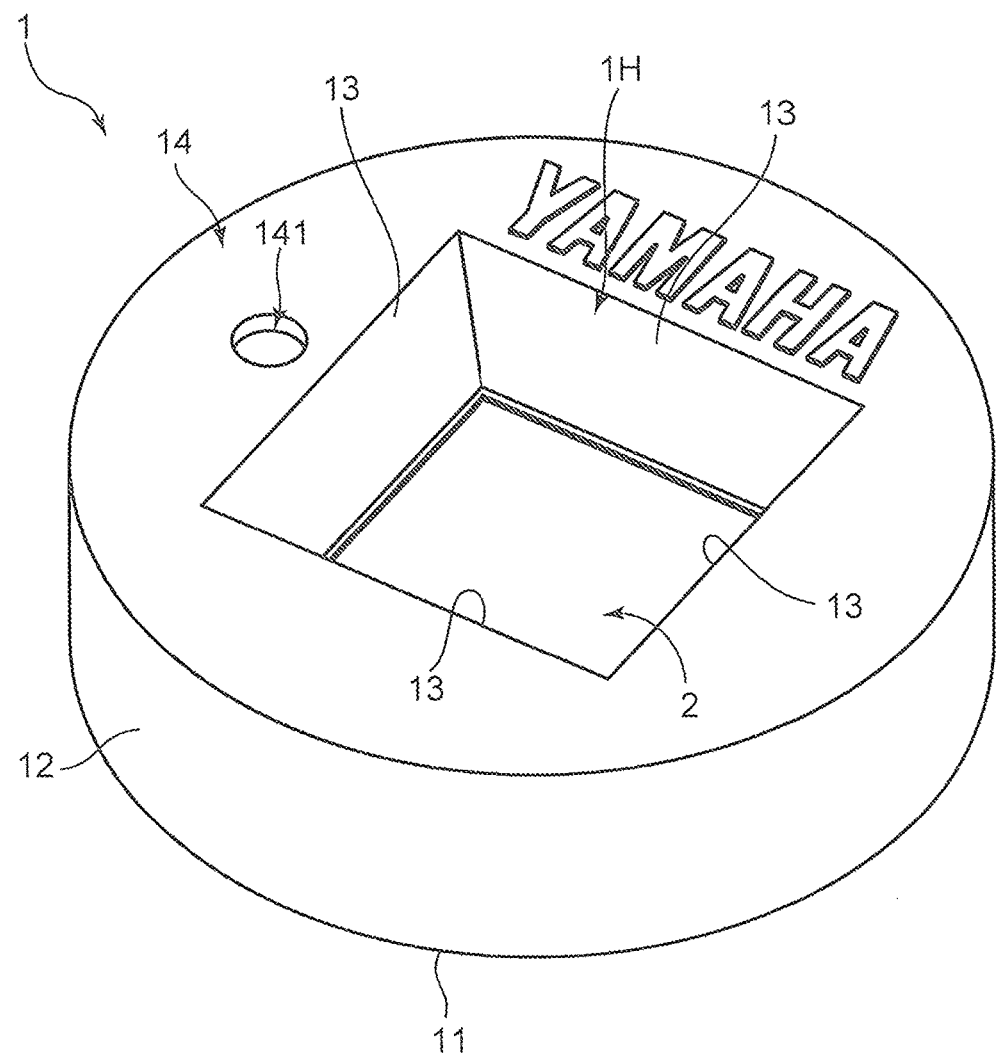
FIG. 2 is a perspective view of a container to be used in the holding device.
Figure 3:
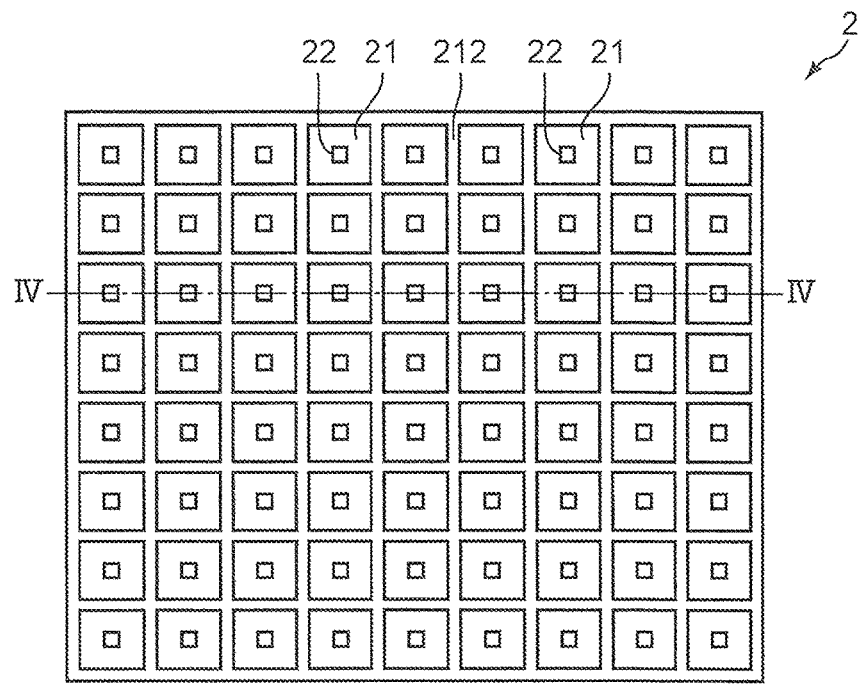
FIG. 3 is a top view of a plate to be used in the holding device.
Figure 4:
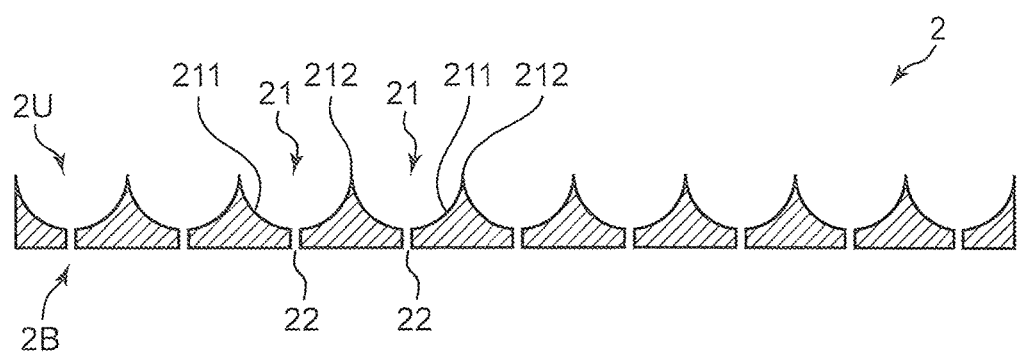
FIG. 4 is a cross-sectional view taken along the line IV-IV of FIG. 3.

FIG. 1 is a side cross-sectional view schematically illustrating an object-holding device D according to the embodiment of the present disclosure. The holding device D includes a container 1 configured to store a liquid L, a plate 2 configured to hold objects (cell aggregates) in the liquid L, and a dispersing mechanism 3 capable of dispersing the cell aggregates on the plate 2. FIG. 2 is a perspective view of the container 1, FIG. 3 is a top view of the plate 2, and FIG. 4 is a cross-sectional view taken along the line Iv-Iv of FIG. 3.

The container 1 has a columnar shape with a rectangular upper opening 1H formed on an upper surface side thereof. The upper opening 1H is an opening for charging cell aggregates and picking up cell aggregates which are sorted out. The shape of the upper opening 1H is not particularly limited, and for example, the upper opening 1H may have a circular shape. The plate 2 is arranged on a lower side of the upper opening 1H. When cell aggregates are to be charged, a dispenser tip 4 that sucks and holds a cell suspension containing the cell aggregates is arranged to be opposed to the upper opening 1H as illustrated in FIG. 1. Then, the cell suspension is discharged from the dispenser tip 4 into the liquid L that is stored in the container 1 without containing cell aggregates.

The liquid L to be stored in the container 1 is not particularly limited as long as the properties of the cell aggregates are not degraded by the liquid L, and may be selected as appropriate depending on the kinds of cell aggregate. Examples of the liquid L may include culture media (cell culture liquids) such as basal media, synthetic media, Eagle's medium, RPMI medium, Fischer's medium, Ham's medium, MCDB medium, and serum as well as cell freezing solutions such as glycerol and Cell Bankers (produced by Juji Field Inc.) to be added before refrigeration storage, formalin, reagents for fluorescent staining, antibodies, purified water, and physiological saline. For example, when BxPC-3 (human pancreatic adenocarcinoma cell), which is a biological cell, is used as the cell aggregate, a mixture of RPMI-1640 medium with 10% of fetal bovine serum (FBS), to which a supplement such as antibiotic or sodium pyruvate is added as necessary, may be used as the liquid L.

The shape of the container 1 is not particularly limited. In this case, a flat, columnar container having a width (diameter) relatively larger than a height is exemplified as the container 1 from the viewpoint of operability, stability, and the like. It is desired that the container 1 be manufactured of a translucent resin material or glass. Thus, the cell aggregates held on the plate 2 can be observed with a camera or the like arranged below the container 1.

The container 1 includes a bottom wall 11, an outer peripheral wall 12, inner peripheral walls 13, and a top wall 14. The bottom wall 11 is a flat disc member that defines a bottom portion of the container 1. The outer peripheral wall 12 is a cylindrical member provided upright on the bottom wall 11. The inner peripheral walls 13 form a rectangular tube-like member arranged at an inner part of the outer peripheral wall 12. The top wall 14 is a plate member that covers a region other than the upper opening 1H on the upper surface side of the container 1.

The outer peripheral wall 12 includes an upper edge portion 121 continuously provided to an outer peripheral edge of the top wall 14, and a lower edge portion 122 continuously provided to an outer peripheral edge of the bottom wall 11. Each of the inner peripheral walls 13 is inclined so that the opening area gradually decreases from the upper opening 1H toward the bottom wall 11. Upper end portions 131 of the inner peripheral walls 13 define the upper opening 1H, and are continuously provided to an inner peripheral edge of the top wall 14. That is, the upper end portions 131 of the inner peripheral walls 13 are continuously provided to the upper edge portion 121 of the outer peripheral wall 12 via the top wall 14 so that the inner peripheral walls 13 are supported by the outer peripheral wall 12. Lower end portions 132 of the inner peripheral walls 13 hold an outer peripheral edge of the plate 2. A working hole 141 being a vertical through hole is formed through the top wall 14. Through the working hole 141, work of, for example, pouring the liquid L into a cavity of the container 1, pouring chemicals into the cavity, or sucking the liquid L from the cavity is performed. Further, in this embodiment, the working hole 141 is also used as a connection port for a pipe to be used for performing air pressure regulation in the cavity.

The plate 2 is a rectangular plate-like member having an upper surface 2U and a lower surface 2B. The plate 2 is held by the lower end portions 132 of the inner peripheral walls 13 in a state in which the lower surface 2B is spaced away from the bottom wall 11 of the container 1. The plate 2 is immersed into the liquid L in the container 1. That is, the liquid L is poured into the container 1 so that the upper surface 2U of the plate 2 is positioned below a liquid surface LT of the liquid L.

The plate 2 includes a plurality of holding portions 21 arranged on the upper surface 2U side and configured to carry cell aggregates, and through holes 22 formed at positions at which the respective holding portions 21 are arranged and linearly passing through the holding portions 21 from the upper surface 2U to the lower surface 2B. In this embodiment, an example in which the holding portions 21 each having a quadrangular shape in top view are arrayed in a matrix is described. The quadrangular shape is one example, and the shape of the holding portion 21 in top view may be, for example, a circular, triangular, pentagonal, or hexagonal shape, or those shapes may be arranged in a honeycomb, linear, or random pattern. Alternatively, the plate 2 may include a single holding portion 21 alone. Note that, similarly to the container 1, it is desired that the plate 2 be formed of a transparent member in order to enable imaging of the carried cell aggregates from the lower surface 2B side.

As illustrated in FIG. 4, the vertical cross-sectional shape of the holding portion 21 is a concave surface 211 (recess) opened upward. The opening of the through hole 22 on the upper surface 2U side is arranged on a bottom surface (deepest position) of the concave surface 211 of the holding portion 21. Upper edge portions 212 of one holding portion 21 and the adjacent holding portion 21 (concave surface 211) are located close to each other. FIG. 3 illustrates the upper edge portion 212 to have a relatively large width in order to emphasize the shape of each holding portion 21, but in actuality, the upper edge portions 212 are adjacent to each other as illustrated in FIG. 4. Therefore, the ridge part formed by contact between the upper edge portions 212 of the adjacent concave surfaces 211 is a sharp projecting part. In a holding portion 21 according to a modified embodiment, a linear inclined wall surface or a stepped wall surface, which is formed so that the opening area of the holding portion 21 decreases from the upper side toward the lower side, is provided in place of the concave surface 211. Alternatively, the holding portion 21 may be formed of a cylindrical or rectangular tube-like recess having a constant opening area from the upper side toward the lower side, or may be formed of a recess in which the upper part is the cylindrical or rectangular tube-like wall surface having a constant opening area and the lower part is a concave surface, an inclined wall surface, or a stepped wall surface.

The holding portion 21 is generally intended to house one cell aggregate. Instead, a designated number of cell aggregates may be housed in one holding portion 21, or a designated amount (total volume or total area) of cell aggregates may be housed in one holding portion 21. The size of the through hole 22 is selected so as to prevent a desired size of a cell aggregate from passing therethrough and allow cell aggregates that are smaller than the desired size and impurities to pass therethrough. A sufficient height to deposit the impurities and the like on the bottom wall 11 is selected as the distance between the lower surface 2B of the plate 2 and the bottom wall 11 of the container 1.

A closed region CA, which is surrounded by the bottom wall 11, the outer peripheral wall 12, the inner peripheral walls 13, and the top wall 14 of the container 1 and the plate 2, is formed in the container 1. The closed region CA and the outside communicate with each other by the working hole 141 and the through holes 22 described above. In a state in which the container 1 stores the liquid L so that the liquid surface LT of the liquid L is positioned above the plate 2 (FIG. 1 illustrates this state) and the working hole 141 is sealed, the through holes 22 are closed by the liquid L retained on the plate 2 so that the closed region CA becomes a sealed region.

The dispersing mechanism 3 is a mechanism for forming, in the through holes 22, liquid flows LC, which flow from the lower surface 2B side toward the upper surface 2U side to raise cell aggregates carried on the holding portions 21. The mechanism for generating the liquid flow LC is not limited, and for example, an air pressure, a water pressure (liquid pressure), or a wave may be used. As described above, in the state in which the container 1 stores the liquid L up to a predetermined height, the closed region CA becomes a sealed region. Thus, when the volume of an air layer is increased or a pressurization force for applying, to the liquid L, a force in a direction of raising the liquid surface LT is generated in the closed region CA, the power thereof is released only to the through hole 22, and hence the liquid flow LC is generated. Specific examples of the dispersing mechanism 3 are described later.

Figure 5:
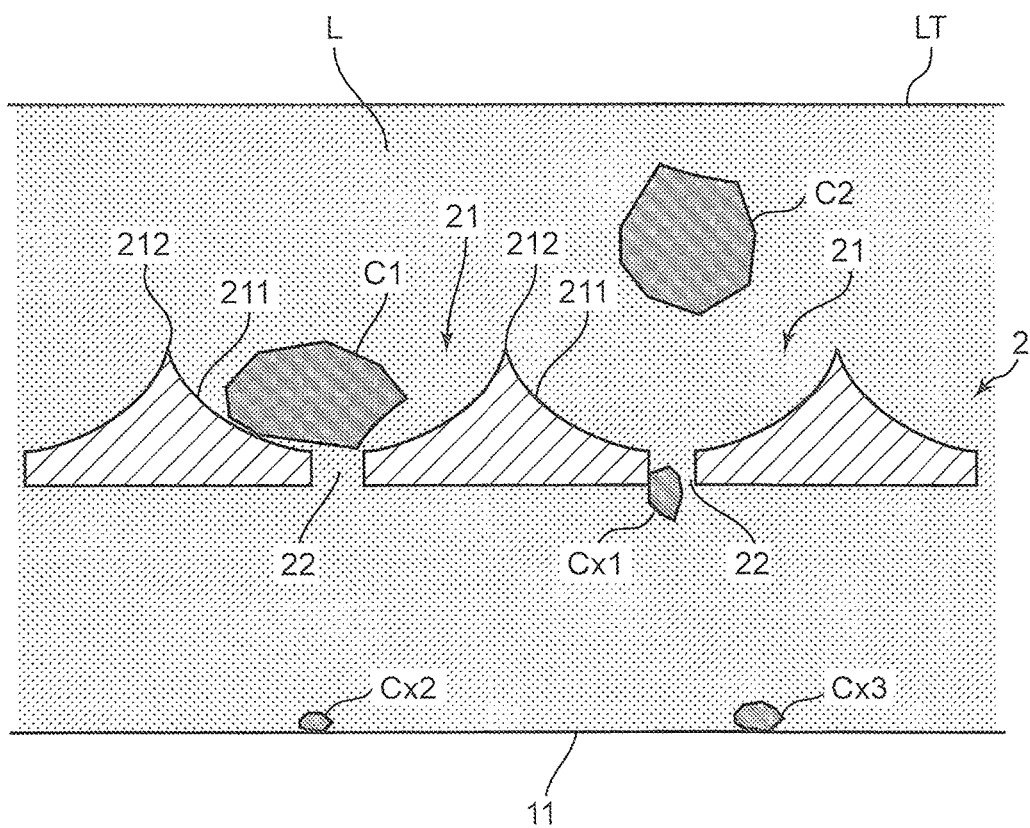
FIG. 5 is a schematic view illustrating how cell aggregates (objects) are carried on the plate.

FIG. 5 is a schematic view for describing how cell aggregates are carried on the plate 2. The work of carrying cell aggregates in this case is also work of sorting out desired cell aggregates from various cell aggregates and impurities. When the cell sorting operation is to be performed, the liquid L (cell culture liquid) containing no cell aggregates is poured into the container 1 through the working hole 141. As a matter of course, the liquid L may be poured from the upper opening 1H of the container 1. The height of the liquid surface LT of the liquid L is set as a height at which the plate 2 is completely immersed into the liquid L. After that, a cell suspension containing cell aggregates C to be sorted and impurities Cx, which are inevitably mixed therein, is poured from the dispenser tip 4 toward the liquid surface LT above the plate 2 through the upper opening 1H of the container 1.

The cell aggregates C and the impurities Cx contained in the poured cell suspension precipitate downward from the liquid surface LT in the liquid L due to the self-weight. FIG. 5 schematically illustrates two cell aggregates C1 and C2 and three impurities Cx1, Cx2, and Cx3. In the large number of holding portions 21 provided to the plate 2, hemispherical cavities (concave surfaces 211) are densely arrayed, and the ridge (upper edge portion 212) demarcating the holding portions 21 is sharp. Thus, the precipitated cell aggregates C1 and C2 and impurities Cx1, Cx2, and Cx3 are guided into the concave surfaces 211 of some of the holding portions 21 without stagnating in the vicinity of the upper edge portions 212.

The cell aggregates C1 and C2 each having a predetermined size cannot pass through the through holes 22. Thus, the cell aggregates C1 and C2 are carried on the holding portions 21 into which the cell aggregates C1 and C2 are guided. On the other hand, the impurities Cx each generally have a much smaller size than the cell aggregates C, and can therefore pass through the through holes 22. Thus, the impurities Cx guided into the concave surfaces 211 pass through the through holes 22 to drop onto the bottom wall 11 of the container 1. FIG. 5 illustrates a situation in which the impurity Cx1 is passing through the through hole 22 and the impurities Cx2 and Cx3 have dropped onto the bottom wall 11. In this manner, the cell aggregates C1 and C2 to be sorted are trapped in the holding portions 21 of the plate 2, and the unnecessary impurities Cx1, Cx2, and Cx3 are collected on the bottom wall 11 of the container 1. The cell sorting operation as described above may be executed only once, or may be repeated a plurality of times as necessary.

In one typical usage example of the holding device D, after the cell sorting operation, an image of the plate 2 that carries the cell aggregates C is taken by the camera arranged below the container 1. The acquired image is analyzed so that which of the holding portions 21 in the group of the holding portions 21 arranged in n columns and m rows in a matrix as illustrated in FIG. 3 the cell aggregates C are carried on is specified in the form of coordinate information. On the basis of the carrying situation of the cell aggregates C, which is grasped at this time, it is determined whether or not to pour the cell suspension into the container 1 again. At the same time, a head having cylinder tips mounted thereto and movable in X, Y, and Z directions is prepared. The head is arranged above the upper opening 1H, and the operation of the head is controlled so that the cylinder tips approach the target holding portions 21 on the basis of the coordinate information. Then, the cell aggregates C carried on the holding portions 21 are sucked by the cylinder tips. The sucked cell aggregates C are transported to another Petri dish or well plate by the head, and are discharged thereto.

In the cell sorting operation, a plurality of cell aggregates C may be housed in one holding portion 21. In general, it is desired that one cell aggregate C be held in one holding portion 21 from the viewpoint of observation of the image of the cell aggregate C and easiness of individual suction by the cylinder tip. However, it is difficult to achieve such a desired holding state for the cell aggregates C only through the normal pouring operation for the cell suspension with the dispenser tip 4. Specifically, after the cell suspension is discharged from the dispenser tip 4, the cell aggregates C are carried on the plate 2 depending on natural precipitation. Therefore, in many cases, the cell aggregates C are carried on the plate 2 in a state in which a plurality of cell aggregates C are concentrated, or a large number of holding portions 21 remain with no cell aggregates C held therein. That is, it is difficult to achieve a state in which the cell aggregates C are spread over the plate 2 roughly homogeneously. This problem is solved by the liquid flow LC to be formed by the dispersing mechanism 3.

Figure 6:
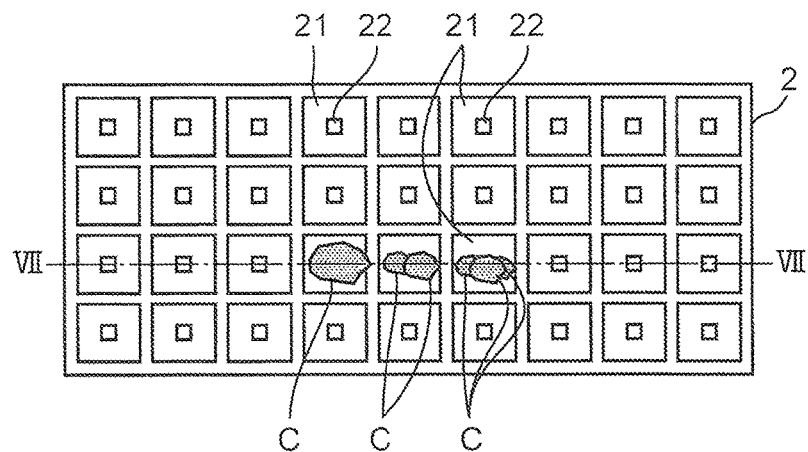
FIG. 6 is a top view of the plate, illustrating a situation in which the cell aggregates are carried on the plate in a concentrated state.
Figure 7:
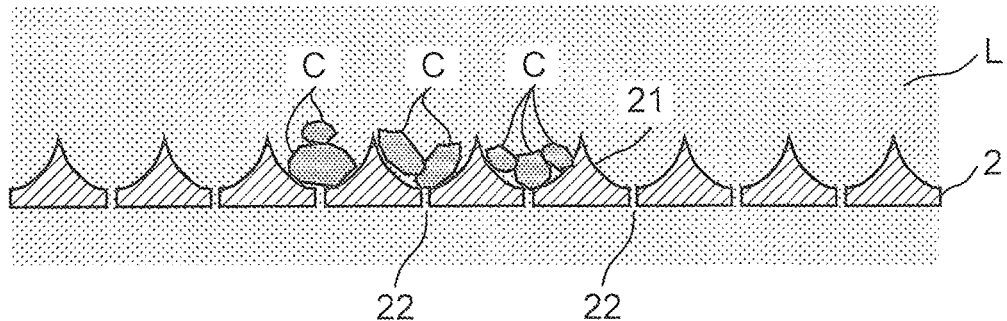
FIG. 7 is a cross-sectional view taken along the line VII-VII of FIG. 6.

FIG. 6 is a top view of the plate, illustrating a situation in which the cell aggregates C are carried on the plate in a concentrated state, and FIG. 7 is a cross-sectional view taken along the line VII-VII of FIG. 6. FIG. 6 and FIG. 7 illustrate a situation in which the cell aggregates C are carried on only three holding portions 21 arranged adjacent to each other on the line VII-VII. Moreover, two or three cell aggregates C are carried on one holding portion 21. In such a carrying state, it is difficult to suck only one cell aggregate C with the cylinder tip. Further, one cell aggregate C and another cell aggregate C overlap with each other as viewed in an up-down direction, and hence overall images of those cell aggregates C cannot be acquired even if the images are taken with the camera from the lower side of the container 1.

Figure 8:
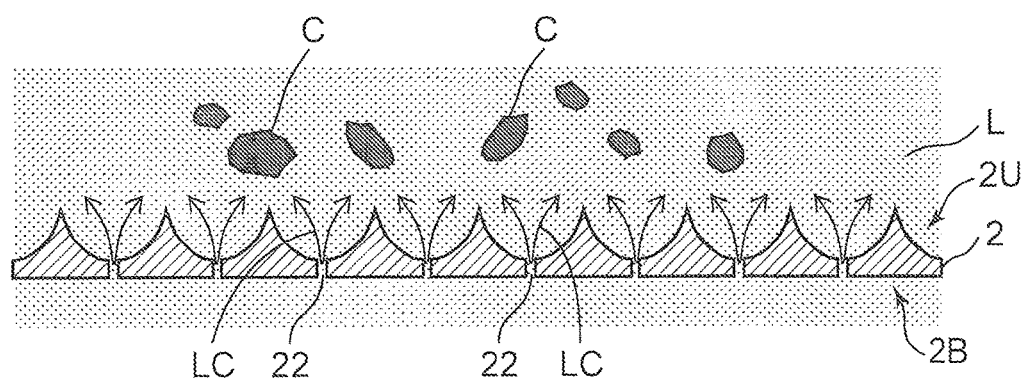
FIG. 8 is a view illustrating a situation in which the cell aggregates on the plate are dispersed by liquid flows.

In this embodiment, in such a case, the liquid flows LC are generated by the dispersing mechanism 3 to resolve the overlapping carrying state of the cell aggregates C. FIG. 8 is a view illustrating a situation in which the cell aggregates C on the plate 2 are dispersed by the liquid flows LC. The liquid flow LC flows through the through hole 22 from the lower surface 2B side of the plate 2 toward the upper surface 2U side thereof. When such a liquid flow LC is generated, the cell aggregates C carried on the holding portion 21 in an overlapping manner are stirred upward (raised). Some of the cell aggregates C deeply enter the hemispherical cavity of the holding portion 21, and are not therefore easily released from the holding portion 21 through application of vibrations to the plate 2 or application of waves from the liquid surface LT side. Even such cell aggregates C can be released from the holding portion 21 by the liquid flow LC jetted from the through hole 22 arranged on the bottom surface of the holding portion 21.

The direction of a push-up force of the liquid flow LC to be received by each cell aggregate C varies depending on the shape and the housing position of the cell aggregate C, and hence the cell aggregates C in a concentrated state are scattered in various directions as illustrated in FIG. 8 to be stirred upward. The period of generation of the liquid flow LC, the flow rate and the amount of the liquid flow LC, and the like are determined as appropriate depending on the characteristics of the cell aggregate C. In short, the period, the flow rate, and the like of the liquid flow LC are not limited as long as the cell aggregate C can temporarily be stirred up into the liquid L above the plate 2. Note that the liquid flow LC generated for an extremely long period or flowing at an extremely high flow rate is not preferred because the cell aggregate C may be damaged. The cell aggregates C stirred up by the liquid flow LC are dispersed in the liquid L, and when the liquid flow LC is stopped, the cell aggregates C start to precipitate due to the self-weight. In order to promote the precipitation, a liquid flow in an opposite direction, that is, a liquid flow which flows from the upper surface 2U side toward the lower surface 2B side may be generated in the through hole 22.

Figure 9A:
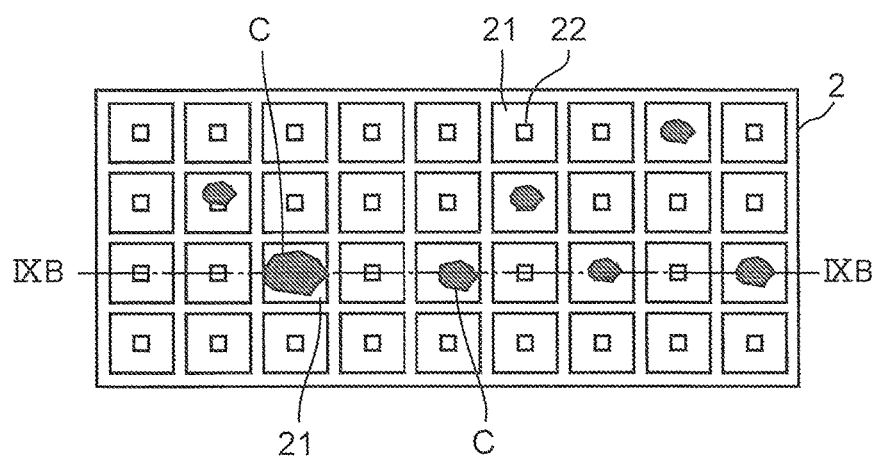
FIG. 9A is a top view of the plate, illustrating a situation in which the dispersed cell aggregates are carried on the plate.
Figure 9B:
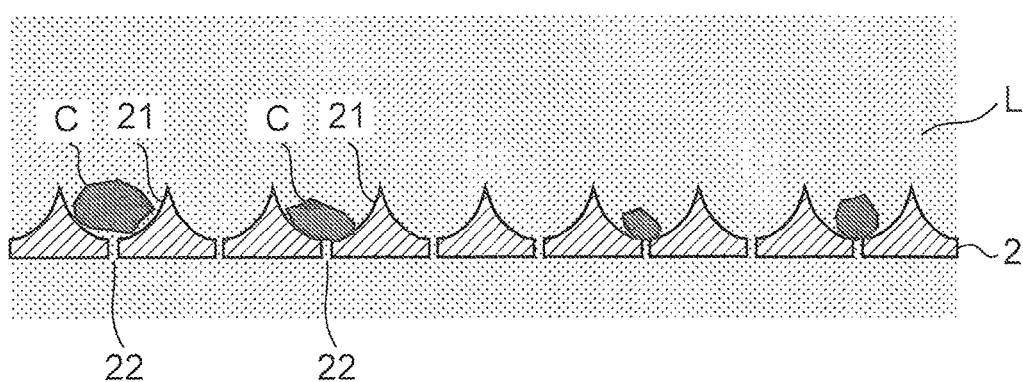
FIG. 9B is a cross-sectional view taken along the line IXB-IXB of FIG. 9A.

FIG. 9A is a top view of the plate, illustrating a situation in which the dispersed cell aggregates C are carried on the plate 2, and FIG. 9B is a cross-sectional view taken along the line IXB-IXB of FIG. 9A. As is apparent from comparison between FIG. 6 and FIG. 9A, the cell aggregates C in a concentrated state are dispersed so that one cell aggregate C is carried on one holding portion 21.

As described above, with the holding device D of this embodiment, the cell aggregates C temporarily carried on the holding portions 21 can be stirred up by the liquid flows LC. Therefore, even if a plurality of cell aggregates C are carried on one holding portion 21, some or all of the cell aggregates C can be stirred up by the liquid flow LC and moved to other holding portions 21. Thus, a large number of cell aggregates C charged into the container 1 can be carried satisfactorily dispersively on the respective holding portions 21 of the plate 2. Accordingly, the suction performance of the cylinder tips for the cell aggregates C and the observability of the cell aggregates C can be obtained satisfactorily. Moreover, the liquid flow LC is generated by using the through hole 22 provided originally to sift the cell aggregates C and the impurities Cx from each other, and hence there is no need to devise a special shape for the plate 2 in order to disperse the cell aggregates C.

Figure 10A:
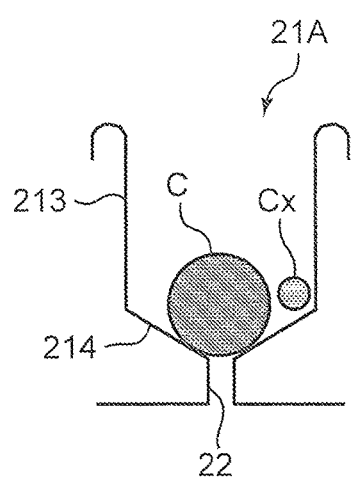
FIGS. 10A to 10C are schematic views illustrating an example of removing an impurity by the liquid flow.
Figure 10B:
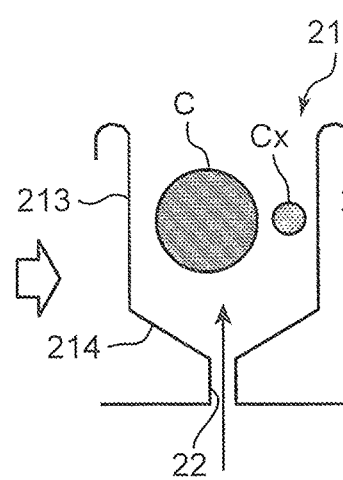
Figure 10C:
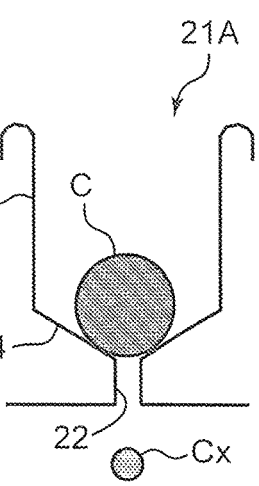

Further, the impurity Cx remaining in the holding portion 21 can be removed by the liquid flow LC described above. This feature is described with reference to FIGS. 10A to 10C. FIGS. 10A to 10C exemplify a holding portion 21A formed of a recess in which the upper part is a tubular portion 213 having a constant opening area and the lower part is an inclined portion 214 having an opening area which decreases toward the through hole 22. The impurity Cx normally drops downward from the through hole 22. However, if the cell aggregate C is housed in the holding portion 21A prior to the drop of the impurity Cx so as to close the through hole 22, or if the cell aggregate C precipitates in a state in which the impurity Cx is placed thereon, the impurity Cx may stagnate in the holding portion 21A. The state of FIG. 10A is an example of the state described above.

The cell aggregate C is held on the inclined portion 214 in a state in which the through hole 22 is closed, and the impurity Cx remains on the side of the cell aggregate C.

In such a case, a minute liquid flow LC is generated in the through hole 22 to enable removal of the impurity Cx from the holding portion 21A. The state of FIG. 10B is a state in which the minute liquid flow LC is generated in the through hole 22 in the state of FIG. 10A. As the liquid flow LC, a liquid flow having such a force that the cell aggregate C held in contact with the inclined portion 214 is stirred up but is not released from the holding portion 21A is selected. With this liquid flow LC, the cell aggregate C and the impurity Cx are stirred up so that the through hole 22 is opened. Thus, as in the state FIG. 10C, it is possible to achieve a state in which the impurity Cx is dropped from the through hole 22 and only the cell aggregate C is held in the holding portion 21A.

First Embodiment

Figure 11:
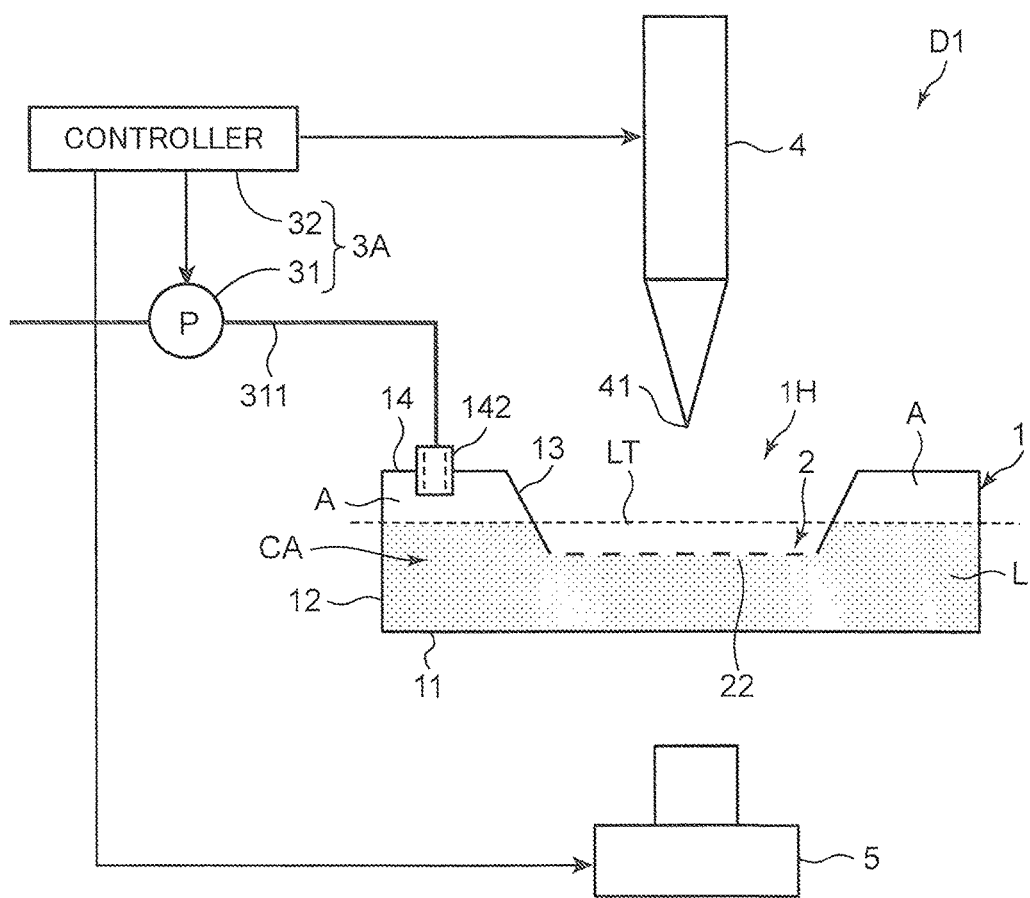
FIG. 11 is a block diagram schematically illustrating an object-holding device according to a first embodiment.

Holding devices D according to several embodiments, including specific examples of the dispersing mechanism 3, are now exemplified. FIG. 11 is a block diagram schematically illustrating an object-holding device D1 according to a first embodiment. The holding device D1 generates a pressurization force in the closed region CA in the container 1 by using an air pressure, thereby generating the liquid flows LC in the through holes 22. The holding device D1 includes a dispersing mechanism 3A (pressure regulator), which is constructed of a pump 31 and a controller 32 therefor, in addition to the container 1 and the plate 2 described above. A camera 5 configured to take an image of the plate 2 is arranged below the container 1. The controller 32 controls not only the discharging operation of the dispenser tip 4 for a cell suspension, but also the imaging operation of the camera 5.

The container 1 is the same as the container 1 which has already been described with reference to FIG. 1 and FIG. 2. The container 1 is also the same in that the liquid L (cell culture liquid containing no cell aggregates C) is poured through the working hole 141 (FIG. 2) in advance, and that the liquid surface LT of the liquid L is set at a height at which the plate 2 is completely immersed and which is lower than the top wall 14 (height in the vicinity of the middle of the inner peripheral wall 13 in the up-down direction). With such a height of the liquid surface LT, a space A in which air is retained (confined) is formed in the closed region CA surrounded by the bottom wall 11, the outer peripheral wall 12, the inner peripheral walls 13, and the top wall 14 of the container 1 and the plate 2. That is, a space A surrounded by the upper parts of the outer peripheral wall 12 and the inner peripheral walls 13, the top wall 14, and the liquid surface LT is formed.

A pipe adapter 142 is mounted to the working hole 141 in the top wall 14. A terminal of an air pipe 311 is mounted to the pipe adapter 142. The pump 31 is a pump built into the middle of the air pipe 311 and capable of operating both in an air suction mode and in an air discharge mode. When the pump 31 is operated in the suction mode, the air in the space A is sucked (negative pressure). On the other hand, when the pump 31 is operated in the discharge mode, the air is sent into the space A (pressurization). The controller 32 controls switching between the suction mode and the discharge mode, and the air suction/discharge amount in each mode.

Although the dispenser tip 4 is simply illustrated in FIG. 11, the dispenser tip 4 includes a syringe capable of sucking and storing a cell suspension, a piston rod configured to move up and down in the syringe, and a drive motor configured to drive the piston rod. By raising the piston rod, the cell suspension is sucked into the syringe from a distal opening 41, and by lowering the piston rod, the cell suspension is discharged from the distal opening 41. The controller 32 controls the operation of the drive motor, thereby controlling the suction and discharge of the cell suspension from the distal opening 41.

The camera 5 is arranged in order to image the plate 2 and the cell aggregates C carried on the plate 2. In this embodiment, each of the container 1 and the plate 2 is formed of a transparent member. The controller 32 has a function of controlling the imaging operation of the camera 5, and a function of analyzing the image taken by the camera 5. Specifically, the controller 32 performs the process of specifying, on the basis of the image, which of the holding portions 21 among the plurality of holding portions 21 arranged in matrix (FIG. 3) the cell aggregates C are carried on, and determining coordinate information on the holding portions 21.

Figure 12A:
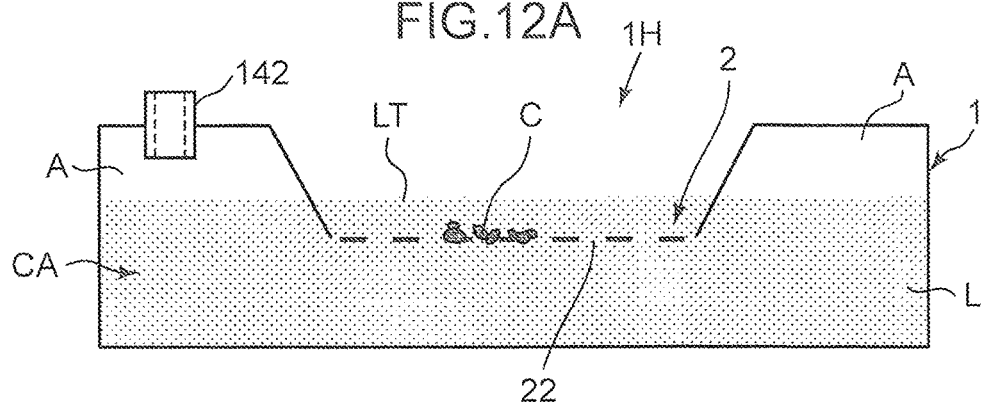
FIG. 12A is a view illustrating a situation in which cell aggregates are charged into a container in the holding device of the first embodiment.

Next, a dispersing operation of the holding device D1 for the cell aggregates C is described. FIG. 12A is a view illustrating a situation in which the cell aggregates C are charged into the container 1 from the upper opening 1H by the dispenser tip 4 in the holding device D1. In FIG. 12A, illustration of the air pipe 311 and the pump 31 is omitted. When the cell aggregates C are to be charged, the space A is opened to the atmosphere. That is, neither of the pressurization force and the suction force acts on the space A. Therefore, the height of the liquid surface LT is not raised by an action of surface tension in the closed region CA, and is therefore constant in the closed region CA and the upper opening 1H. In the state of FIG. 12A, similarly to the case which has already been described with reference to FIG. 6 and FIG. 7, the cell aggregates C are carried while being concentrated on a narrow region on the plate 2.

Figure 12B:
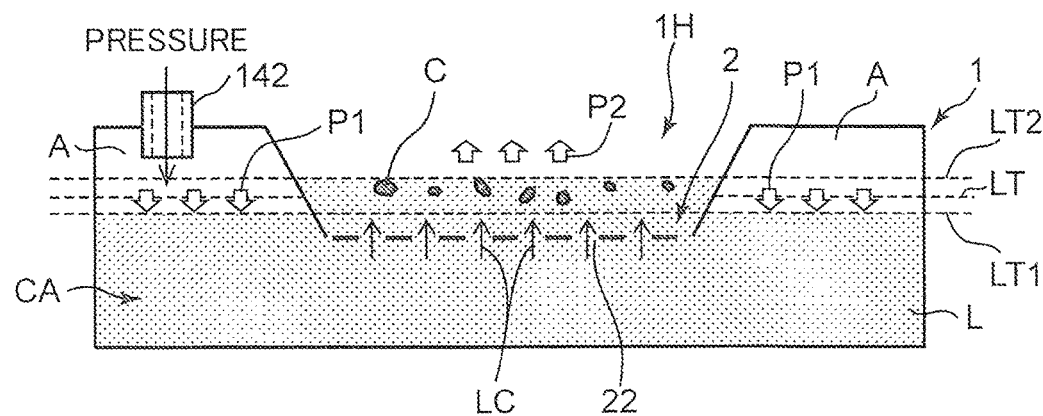
FIG. 12B is a view illustrating a situation in which liquid flows are generated through pressure application so that the cell aggregates are stirred up.

FIG. 12B is a view illustrating a situation in which the liquid flows LC are generated through pressure application to the space A so that the cell aggregates C are stirred up above the plate 2. This situation is a situation immediately after the controller 32 operates the pump 31 in the discharge mode so that a predetermined amount of air is sent into the space A through the pipe adapter 142. Through this sending of the air, the inside of the space A is pressurized. The pressure is applied to the liquid surface (liquid surface facing the space A) LT in the closed region CA as indicated by the arrows P1, and hence the level of the liquid surface LT is decreased to a lower level LT1. The pressure of the liquid L that has received the pressure of the arrows P1 at the liquid surface LT in the closed region CA is released to the through holes 22 of the plate 2. Therefore, the liquid flows LC, which flow through the through holes 22 from the lower side to the upper side, are generated through the application of the pressure of the arrows P1.

Along with the generation of the liquid flows LC, a part of the liquid L flows toward the upper surface side of the plate 2. Thus, as indicated by the arrows P2, the liquid surface LT in the region of the upper opening 1H is raised to an upper level LT2. Further, the liquid flows LC cause the cell aggregates C carried on the plate 2 to be stirred upward in the liquid L at the upper level LT2 above the plate 2. Thus, the cell aggregates C in a concentrated state are dispersed.

After that, the controller 32 stops the pump 31 and controls a valve device (not shown), thereby canceling the pressurized state in the space A. Thus, the space A gradually recovers an outside air pressure. The liquid surface LT at the upper level LT2 in the region of the upper opening 1H is lowered, and the liquid surface LT at the lower level LT1 in the closed region CA is raised. Then, as in the state of FIG. 12A, the liquid surface LT has a constant level over the entire container 1. Then, the stirred-up cell aggregates C precipitate due to the self-weight, and are then carried on the plate 2 (holding portions 21). If the precipitation after the dispersion depends on natural precipitation of the cell aggregates C, the dispersing operation is finished at this point.

After the precipitation, the controller 32 operates the camera 5 to take an image of the plate 2 that carries the cell aggregates C. Further, the controller 32 analyzes the image taken by the camera 5 to derive information (coordinate information) for specifying the carrying positions of the cell aggregates C on the plate 2. Note that, when the dispersion of the cell aggregates C is insufficient as a result of the image analysis, that is, when it is confirmed in the image that a large number of cell aggregates C overlap with each other, the controller 32 executes the dispersing operation again.

Figure 12C:
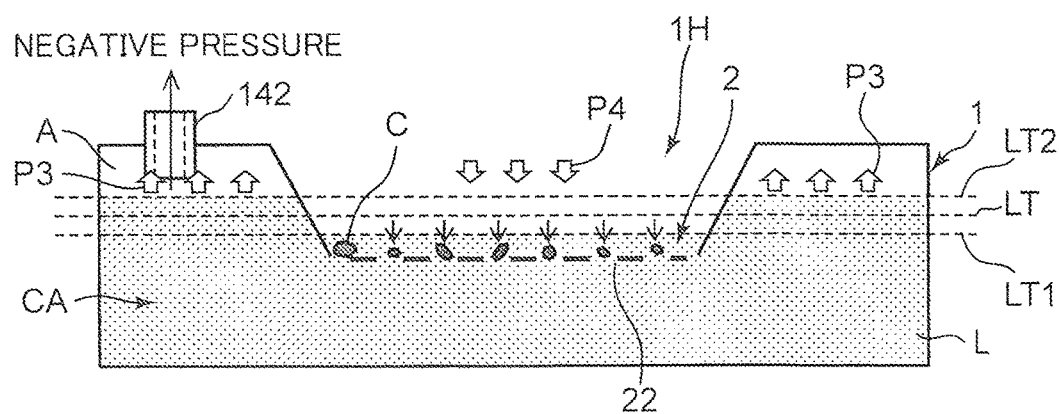
FIG. 12C is a view illustrating a situation in which the cell aggregates precipitate on the plate while being assisted by a negative pressure.

When the rate of natural precipitation of the cell aggregates C is low, it is desired that the precipitation be promoted by setting the space A to have a negative pressure. The dispersing mechanism 3A of this embodiment further has a function of depressurizing the space A after the pressurization of the space A is executed as described above. FIG. 12C is a view illustrating a situation in which the cell aggregates C precipitate on the plate 2 while being assisted by a negative pressure. This situation is a situation in which the controller 32 operates the pump 31 in the suction mode so that the air in the space A is sucked through the pipe adapter 142 and therefore the space A is depressurized.

When the space A is set to have the negative pressure, the liquid surface LT in the closed region CA is raised as indicated by the arrows P3. Thus, liquid flows in a direction opposite to that of the liquid flows LC (FIG. 12B) are generated in the through holes 22, and the liquid surface LT in the region of the upper opening 1H is lowered as indicated by the arrows P4. Then, the cell aggregates C are sucked into the through holes 22 by the liquid flows in the opposite direction, thereby promoting the precipitation onto the plate 2. After the precipitation, the controller 32 stops the pump 31 and controls the valve device (not shown), thereby gradually canceling the negative-pressure state in the space A. Then, the liquid surface LT returns to a state of a constant level over the entire container 1. Whether or not to execute such an assist of the precipitation by the negative pressure is determined in advance depending on the characteristics of the cell aggregates C to be sorted.

In the above, an example in which the cell aggregates C are dispersed by being significantly stirred up above the plate 2 is described. A minute liquid flow LC may be generated to change a posture of the cell aggregate C carried on the holding portion 21. In this embodiment, the cell aggregate C carried on the holding portion 21 can be imaged with the camera 5 arranged below the container 1. However, only one side of the cell aggregate C can be imaged at a low angle, and hence the image is insufficient to recognize an overall image of the cell aggregate C. If the posture of the carried cell aggregate C can be changed, different sides of the cell aggregate C can be imaged.

Figure 13A:
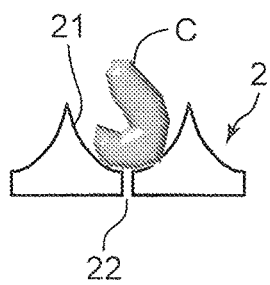
FIGS. 13A to 13E show views illustrating an example of changing, by the liquid flow, a posture of the cell aggregate carried on a holding portion.
Figure 13C:
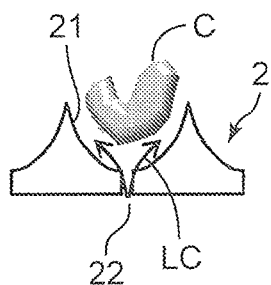
Figure 13D:
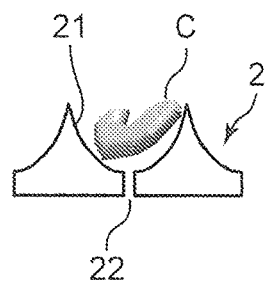
Figure 13B:
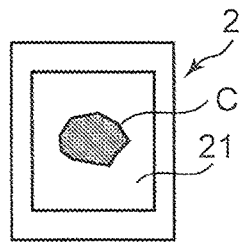

FIGS. 13A to 13E show views illustrating an example of changing, by the liquid flow LC, the posture of the cell aggregate C carried on the holding portion 21. FIG. 13A is a side cross-sectional view illustrating a situation in which one cell aggregate C is carried on one holding portion 21 in a certain posture, and FIG. 13B is a plan view illustrating the carrying state of FIG. 13A as viewed from the lower side of the plate 2 (imaging angle of the camera 5). The 3D shape of the cell aggregate C exemplified in this case is a column curved into a substantially U-shape. However, when the cell aggregate C is carried on the holding portion 21 in an upright state as illustrated in FIG. 13A, the 2D shape observed from the lower side of the plate 2 is a substantially oval shape as illustrated in FIG. 13B. That is, the original shape of the cell aggregate C cannot be grasped.

Therefore, as illustrated in FIG. 13C, the minute liquid flow LC is generated in the through hole 22 to slightly float the cell aggregate C above the holding portion 21, thereby changing the posture of the cell aggregate C. In this case, the controller 32 drives the pump 31 in the discharge mode for a short period of time to apply a pressure analogous to a weak shock wave to the liquid surface LT in the closed region CA. Then, the weak liquid flow LC, which acts for a short period of time in response to the pressure analogous to a shock wave, is generated in the through hole 22.

Figure 13E:
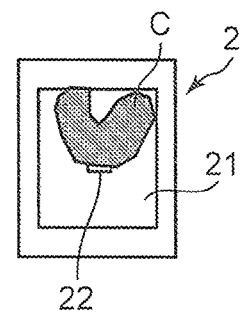

FIG. 13D is a side cross-sectional view illustrating a situation in which the cell aggregate C after the posture is changed is carried on the holding portion 21, and FIG. 13E is a plan view illustrating the carrying state of FIG. 13D as viewed from the lower side of the plate 2. With the 2D shape of FIG. 13E, the feature of the cell aggregate C in terms of the shape can be easily grasped. Further, with the 2D shapes of FIG. 13B and FIG. 13E, the 3D shape of the cell aggregate C can be estimated to some extent.

Figure 14A:
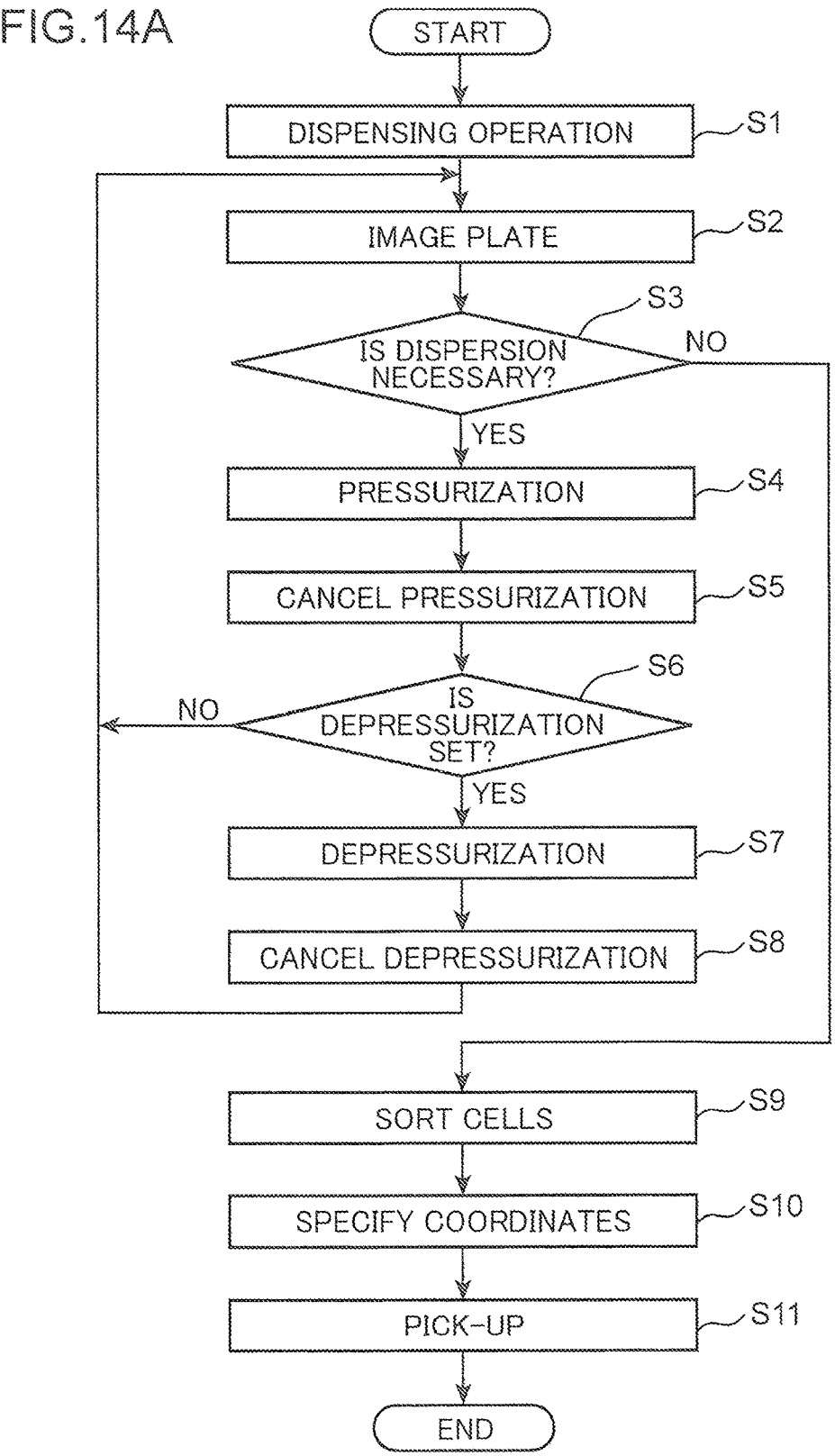
FIG. 14A is a flowchart illustrating an example of a control flow for the holding device, which is executed by a controller.

Next, a control sequence of the controller 32 is described. FIG. 14A is a flowchart illustrating an example of a control flow for the holding device D1, which is executed by the controller 32. The controller 32 operates the dispenser tip 4, which has sucked a cell suspension in advance, to discharge the cell suspension through the upper opening 1H to the container 1 into which the liquid L is poured in advance (Step S1). After the dispensing operation of Step S1, the controller 32 waits for an elapse of a period of time required for precipitation of the cell aggregates C, and operates the camera 5 to take an image of the plate 2 that carries the cell aggregates C (Step S2).

After that, the controller 32 analyzes the image taken by the camera 5 to determine whether or not the dispersing operation for the cell aggregates C is necessary (Step S3). For this determination, for example, an algorithm for specifying the individual cell aggregates C through edge detection on the image to determine the degree of distribution of the individual cell aggregates C is applicable. In another embodiment, there is provided a mode in which the image taken by the camera 5 is displayed on a monitor, the user determines on the monitor whether or not the dispersing operation is necessary, and the controller 32 receives an instruction on the necessity for the dispersing operation. Alternatively, there may be provided a mode in which the dispersing operation is always executed after the dispensing operation without determining whether or not the dispersing operation is necessary.

When it is determined that the dispersing operation is necessary (YES in Step S3), the controller 32 operates the pump 31 in the discharge mode to pressurize the space A of the container 1 (Step S4). Through the pressurizing operation, the liquid flows LC, which flow through the through holes 22 from the lower side to the upper side, are generated so that the cell aggregates C carried on the plate 2 in a concentrated state are stirred upward. The period of time for the pressurizing operation is, for example, about 0.5 seconds to 5 seconds. After that, the controller 32 stops the pump 31 and controls the valve device (not shown), thereby canceling the pressurized state in the space A (Step S5).

Next, the controller 32 checks whether or not depressurization of the space A is set to be executed after the pressurizing operation described above (Step S6). As described above, when the rate of natural precipitation of the cell aggregates C is low, the depressurization is executed. When the depressurization is set to be executed (YES in Step S6), the controller 32 operates the pump 31 in the suction mode to depressurize the space A (Step S7). After a lapse of a predetermined period of time, the controller 32 stops the pump 31 to cancel the depressurized state in the space A (Step S8). After that, the processing returns to Step S2, in which the plate 2 is imaged again to repeat the processing. The same applies to a case where the depressurization is not set to be executed (NO in Step S6).

On the other hand, when it is determined that the dispersing operation is not necessary (NO in Step S3), that is, when it is confirmed that the cell aggregates C are carried on the plate 2 in a satisfactorily dispersed state, cell sorting processing is executed (Step S9). The cell sorting processing is processing of specifying, among the cell aggregates C carried on the plate 2, cell aggregates C that satisfy predetermined criteria. In the cell aggregates C, cell aggregates C having insufficient sizes or distorted shapes are mixed and are not therefore suitable for subsequent cultivation, tests, or the like. In Step S9, the controller 32 analyzes the image acquired in Step S2 to specify acceptable specimens. Alternatively, there may be provided a mode in which the user specifies acceptable specimens on the monitor through visual check and the controller 32 receives an instruction on the specified acceptable specimens.

After that, the controller 32 derives coordinate information for specifying the carrying positions (positions of the holding portions 21) of the cell aggregates C specified as acceptable specimens on the plate 2 (Step S10). Then, a head (not shown) including a plurality of cylinder tips capable of sucking the cell aggregates C is arranged above the upper opening 1H. The cylinder tips are positioned with respect to the cell aggregates C on the basis of the coordinate information, and the cell aggregates C are sucked (picked up) by the respective cylinder tips individually (Step S11). After the pick-up operation is finished, the head is moved toward another Petri dish or well plate to which the cell aggregates C are to be discharged.

FIG. 14B is a flowchart illustrating another example of the control flow for the holding device D1, which is executed by the controller 32. In this example, a sequence in which the cell aggregates C which can be picked up after the dispensing operation are first picked up from the plate 2 and then the dispersing operation is executed is described. The controller 32 operates the dispenser tip 4 to discharge the cell suspension to the container 1 (Step S21). After the precipitation of the cell aggregates C, the controller 32 operates the camera 5 to take an image of the plate 2 that carries the cell aggregates C (Step S22).

On the basis of the acquired image, the controller 32 specifies the cell aggregates C which can be picked up. Specifically, the holding portions 21 each carrying only one cell aggregate C that satisfies the conditions for acceptable specimens are specified. Then, coordinate information on the specified holding portions 21 is derived (Step S23). On the basis of the coordinate information, the cell aggregates C being acceptable specimens are picked up from the plate 2 by the cylinder tips (Step S24).

Next, the controller 32 analyzes the image acquired in Step S22 or an image newly taken after the execution of Step S24 to determine whether or not the dispersing operation for the cell aggregates C is necessary (Step S25). If the dispensing operation of Step S21 is satisfactorily performed so that the dispersing state of the cell aggregates C is satisfactory and therefore a necessary number of cell aggregates C can be picked up in Step S24, it is determined that the dispersing operation is not necessary. When it is determined that the dispersing operation is necessary (YES in Step S25), that is, when the cell aggregates C are carried in an overlapping manner, the controller 32 operates the pump 31 in the discharge mode to pressurize the space A of the container 1 (Step S26). Through the pressurizing operation, the liquid flows LC, which flow through the through holes 22 from the lower side to the upper side, are generated so that the cell aggregates C are dispersed. After an elapse of a predetermined period of time, the controller 32 cancels the pressurized state in the space A (Step S27).

Next, the controller 32 checks whether or not depressurization of the space A is set to be executed after the pressurizing operation described above (Step S28). When the depressurization is set to be executed (YES in Step S28), the controller 32 operates the pump 31 in the suction mode to depressurize the space A (Step S29). After an elapse of a predetermined period of time, the controller 32 stops the pump 31 to cancel the depressurized state in the space A (Step S30). After that, the processing returns to Step S22, in which the plate 2 is imaged again to repeat the processing. The same applies to a case where the depressurization is not set to be executed (NO in Step S28). Thus, the cell aggregates C which can be picked up through the dispersing operation are picked up in Step S24.

On the other hand, when it is determined that the dispersing operation is not necessary (NO in Step S25), it is determined whether or not to also perform the dispensing operation (Step S31). The description "the dispersing operation is not necessary" herein encompasses a case where the cell aggregates C to be picked up no longer exist even if the dispersing operation is performed a plurality of times. For example, it is determined that additional dispensing is necessary when the number of cell aggregates C specified as acceptable specimens is smaller than a prescribed value (YES in Step S31), and the processing returns to Step S21, in which the additional dispensing operation is executed. On the other hand, when it is determined that the additional dispensing is not necessary (NO in Step S31), the controller 32 ends the processing.

Second Embodiment

Figure 15:
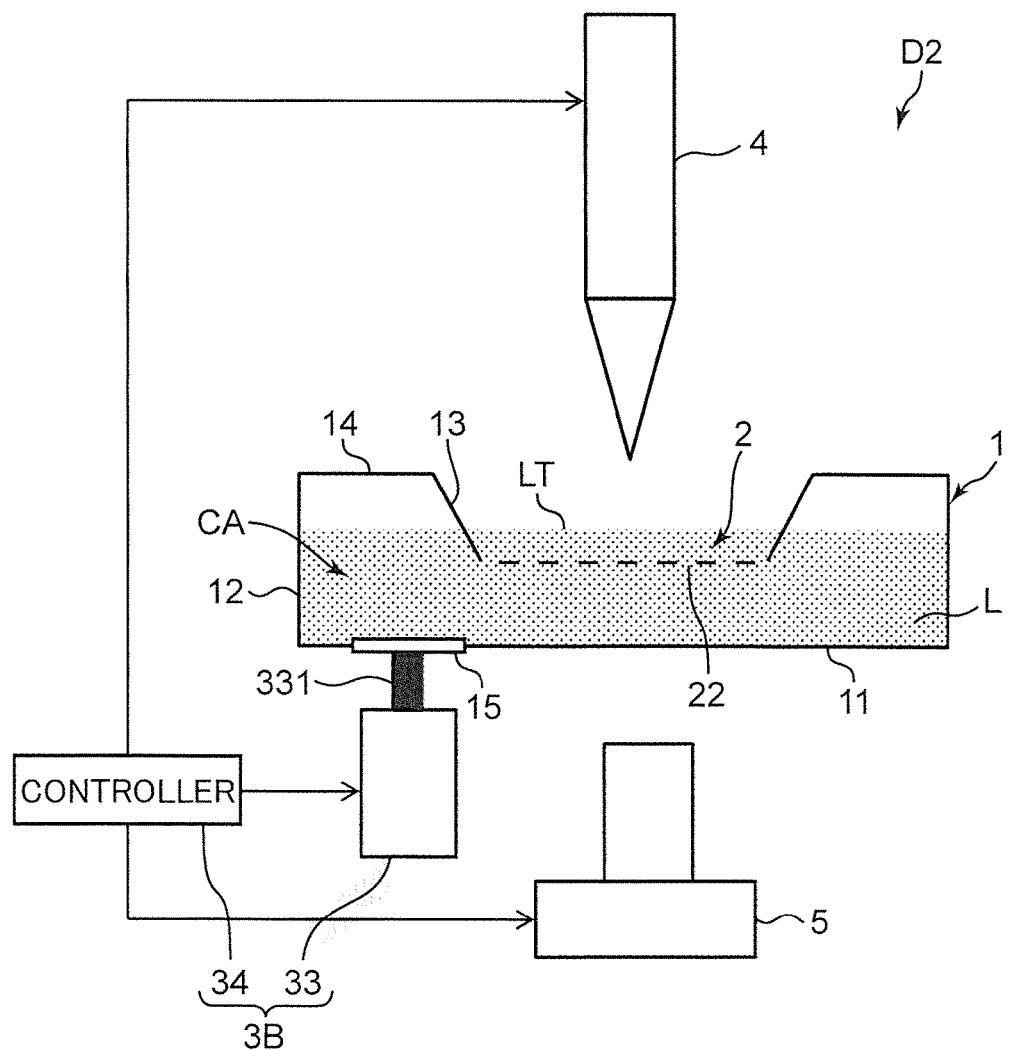
FIG. 15 is a block diagram schematically illustrating an object-holding device according to a second embodiment.

FIG. 15 is a block diagram schematically illustrating an object-holding device D2 according to a second embodiment. The holding device D2 applies a pressure to the liquid L by a diaphragm-type dispersing mechanism 3B, thereby generating the liquid flows LC in the through holes 22. The dispersing mechanism 3B includes a drive mechanism 33 including an actuator rod 331, and a controller 34 therefor. A part of the bottom wall 11 of the container 1 is formed of an elastically-deformable diaphragm 15 (bulging member). The actuator rod 331 is arranged in contact with the diaphragm 15. In the second embodiment, the working hole 141 is not used at the time of dispersion, and hence illustration of the working hole 141 is omitted in FIG. 15. The other configuration is the same as that of the first embodiment.

The drive mechanism 33 only needs to be capable of protruding and retracting the actuator rod 331, and for example, a hydraulic mechanism, a pneumatic mechanism, a solenoid actuator, or an electric actuator using a drive motor may be employed. The diaphragm 15 is formed of an elastic thin film made of rubber or resin, and is attached to the bottom wall 11 so as to close an opening provided in the bottom wall 11 of the container 1. The diaphragm 15 is capable of changing a state thereof between a bulging state, in which the diaphragm 15 is pressed by the actuator rod 331 to bulge in the liquid L which is present in the closed region CA in the container 1, and a retreating state, in which the pressing by the actuator rod 331 is released to terminate the bulging.

Figure 16A:
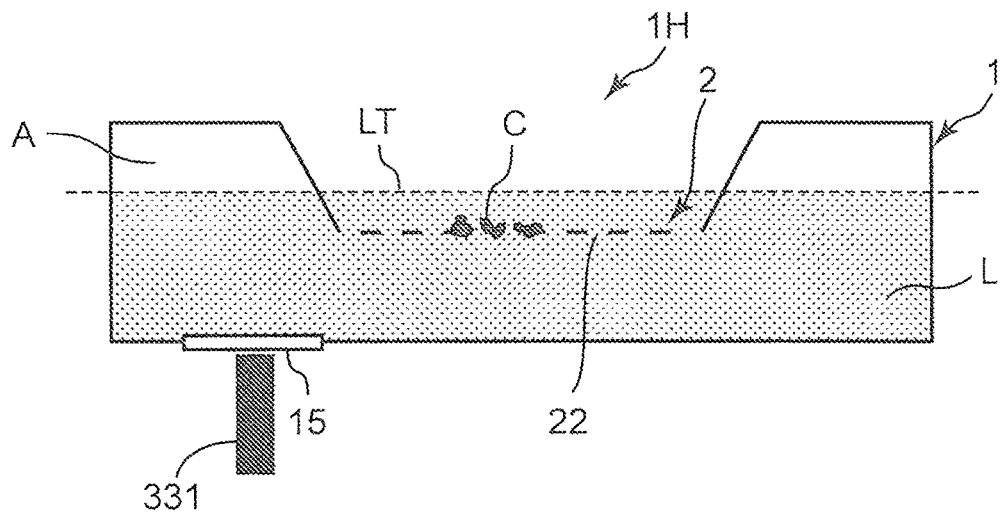
FIG. 16A is a view illustrating a situation in which cell aggregates are charged into a container in the holding device of the second embodiment.

FIG. 16A is a view illustrating a situation in which the cell aggregates C are charged into the container 1 from the upper opening 1H by the dispenser tip 4 in the holding device D2. When the cell aggregates C are to be charged, the controller 34 does not operate the drive mechanism 33. That is, the actuator rod 331 is not protruded so that the diaphragm 15 is brought into the retreating state. In the state of FIG. 16A, the cell aggregates C are carried while being concentrated on a narrow region on the plate 2.

Figure 16B:
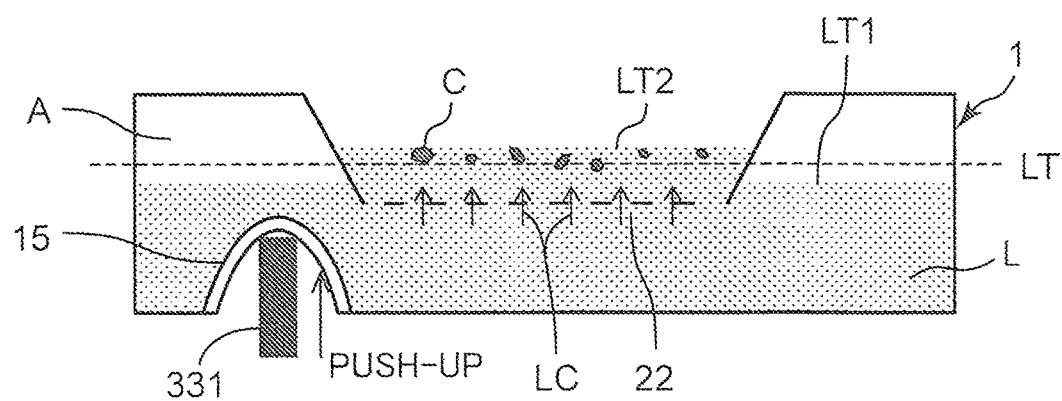
FIG. 16B is a view illustrating a situation in which liquid flows are generated through pressure application so that the cell aggregates are stirred up.

FIG. 16B is a view illustrating a situation in which the liquid flows LC are generated through pressure application from the diaphragm 15 so that the cell aggregates C are stirred up above the plate 2. This situation is a situation in which the controller 34 operates the drive mechanism 33 to protrude the actuator rod 331. The protrusion of the actuator rod 331 causes the diaphragm 15 to be pushed upward. Thus, a pressure is applied to the liquid L in the closed region CA. The pressure generates the liquid flows LC in the through holes 22 of the plate 2.

Along with the generation of the liquid flows LC, a part of the liquid L flows toward the upper surface side of the plate 2. Thus, the liquid surface LT in the region of the upper opening 1H is raised to the upper level LT2. On the other hand, the liquid surface LT in the closed region CA is lowered to the lower level LT1. Further, the liquid flows LC cause the cell aggregates C carried on the plate 2 to be stirred upward in the liquid L at the upper level LT2 above the plate 2. Thus, the cell aggregates C in a concentrated state are dispersed.

After that, the controller 34 causes the actuator rod 331 to be retracted into the drive mechanism 33, thereby bringing the diaphragm 15 back into the retreating state. Thus, the pressurized state of the liquid L is canceled. The liquid surface LT at the upper level LT2 in the region of the upper opening 1H is lowered, and the liquid surface LT at the lower level LT1 in the closed region CA is raised. Then, as in the state of FIG. 16A, the liquid surface LT has a constant level over the entire container 1. Then, the stirred-up cell aggregates C precipitate due to the self-weight, and are then carried on the plate 2 (holding portions 21).

Third Embodiment

Figure 18A:
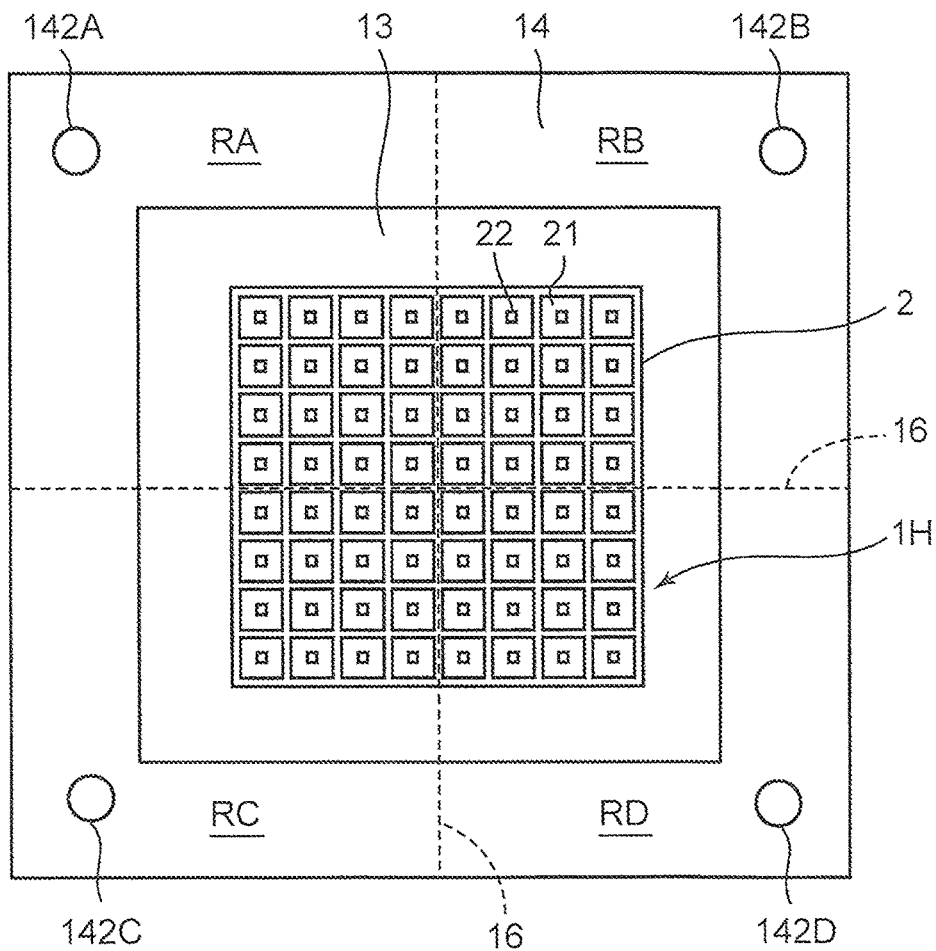
FIG. 18A is a top view of a container to be used in the holding device of the third embodiment.

FIG. 17 is a block diagram schematically illustrating an object-holding device D3 according to a third embodiment, and FIG. 18A is a top view of a container to be used in the holding device D3. The holding device D3 is a holding device according to a modified embodiment of the holding device D1 of the first embodiment. The holding device D3 has a structure capable of partially dispersing the cell aggregates C carried on the plate 2.

A container 1A of the holding device D3 includes partition walls 16 configured to partition the closed region CA in the container 1A into four segments. The partition walls 16 are two rectangular flat plates assembled orthogonal to each other, and therefore have a crossed shape in top view (FIG. 18A). The height of each partition wall 16 is equal to a distance between the bottom wall 11 of the container 1A and the plate 2. With such partition walls 16, the closed region CA is partitioned into a first segment RA, a second segment RB, a third segment RC, and a fourth segment RD, and the liquid L which is present in each segment does not directly flow into the other segments. However, the respective segments indirectly communicate to each other through an upper liquid layer LS, which is present above the plate 2 in the region corresponding to the upper opening 1H, and the through holes 22 of the plate 2.

Figure 18B:
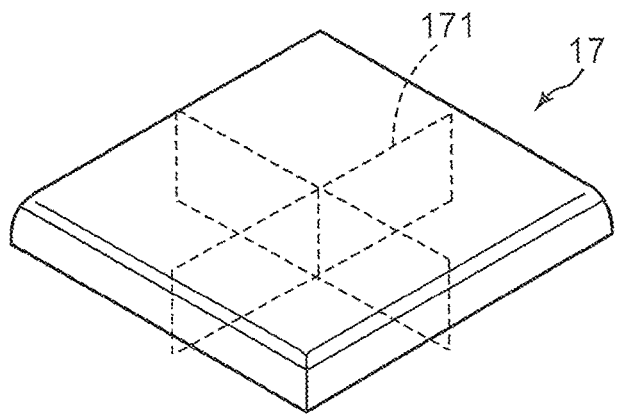
FIG. 18B is a perspective view of a lid member to be fitted into an upper opening of the container.

Note that a partition adapted to the segments defined by the partition walls 16 may also be provided in the upper liquid layer LS. FIG. 18B is a perspective view of a lid member 17 to be fitted into the upper opening 1H of the container 1A. The lid member 17 is a box-like member opened in a lower surface thereof to have substantially the same size as the plate 2 in top view. Partition plates 171 having a crossed shape are provided inside the lid member 17. The lower end edges of the partition plates 171 are brought into contact with the upper surface 2U (upper edge portions 212) of the plate 2, and the upper end edges of the partition plates 171 are located higher than the liquid surface in the upper liquid layer LS. The partition plates 171 have a crossed shape conforming to the segments of the partition walls 16, and are arranged directly above the partition walls 16. By fitting such a lid member 17 into the upper opening 1H, each of the first, second, third, and fourth segments RA, RB, RC, and RD can be made completely independent of the other segments. The lid member 17 is useful, for example, when chemicals different in components or density are added to the respective segments after the dispensing.

Working holes are provided in the top wall 14 at portions corresponding to the positions of the first, second, third, and fourth segments RA, RB, RC, and RD, respectively, and pipe adapters 142A, 142B, 142C, and 142D are mounted to those working holes, respectively. Terminals of air pipes are mounted to the pipe adapters, respectively. FIG. 17 illustrates first and second air pipes 311A and 311B mounted to the pipe adapters 142A and 142B in the first and second segments RA and RB, respectively.

The holding device D3 includes dispersing mechanisms 3C for the first, second, third, and fourth segments RA, RB, RC, and RD in addition to the container 1A and the plate 2 described above. FIG. 17 illustrates the dispersing mechanisms 3C for the first and second segments RA and RB. The dispersing mechanism 3C for the first segment RA includes a first pump 35A and a first valve device 36A mounted to the first air pipe 311A. The dispersing mechanism 3C for the second segment RB includes a second pump 35B and a second valve device 36B mounted to the second air pipe 311B. The pumps 35A and 35B and the valve devices 36A and 36B are controlled by a common controller 37. The same applies to the dispersing mechanisms 3C for the third and fourth segments RC and RD.

The first and second pumps 35A and 35B are pumps capable of operating both in the air suction mode and in the air discharge mode. The first and second valve devices 36A and 36B are valves provided in proximity to the pipe adapters 142A and 142B and configured to open and close the first and second air pipes 311A and 311B, respectively. The controller 37 controls switching between the suction mode and the discharge mode of the first and second pumps 35A and 35B, and the air suction/discharge amount in each mode. Further, the controller 37 controls the first and second valve devices 36A and 36B to be opened and closed independently as necessary.

Figure 19:
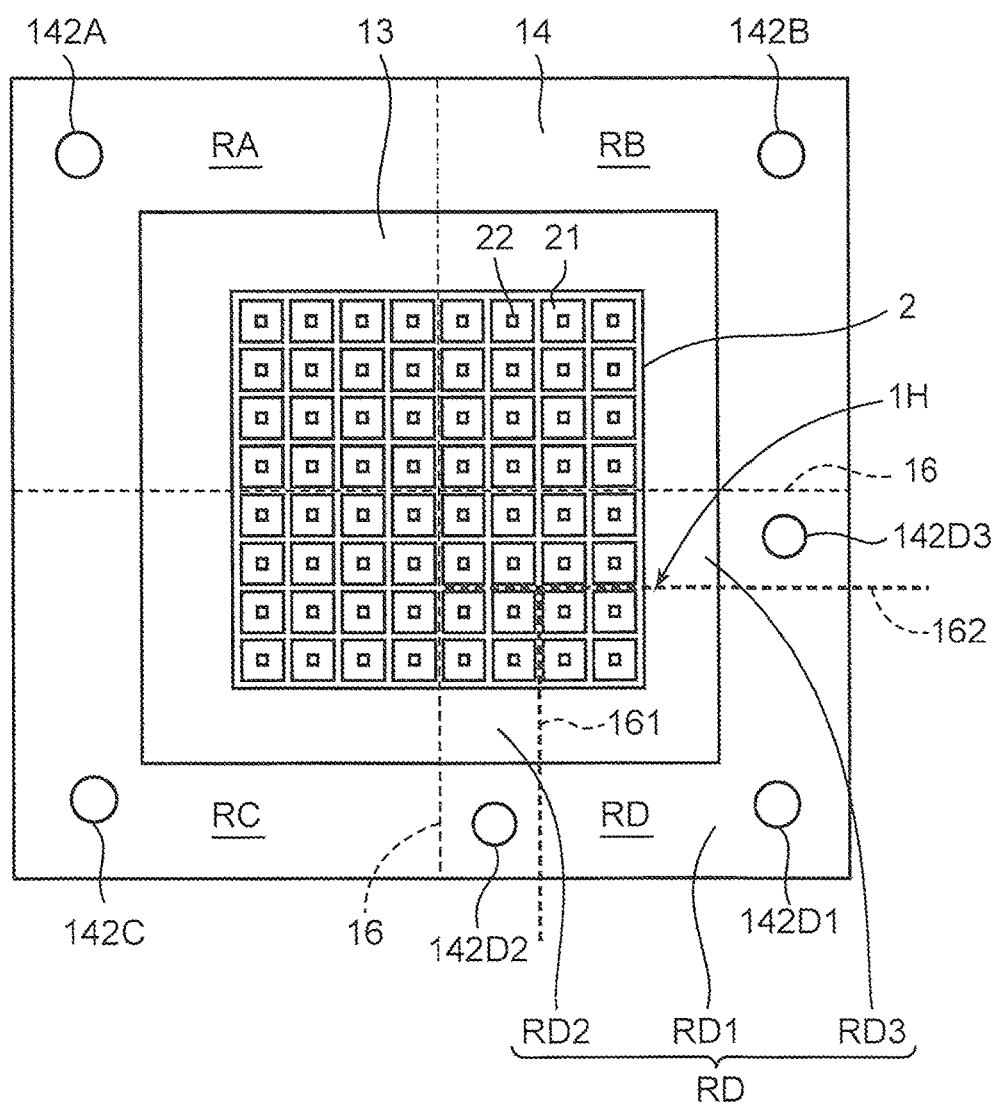
FIG. 19 is a top view of a container to be used in a holding device according to a modified embodiment of the third embodiment.

Note that the first, second, third, and fourth segments RA, RB, RC, and RD may be sub-partitioned into even smaller segments as necessary. FIG. 19 illustrates an example in which the fourth segment RD is sub-partitioned. Sub-partition walls 161 and 162 are arranged in the fourth segment RD to independently form three subsegments, that is, a 41st subsegment RD1, a 42nd subsegment RD2, and a 43rd subsegment RD3. Working holes are provided in the top wall 14 at portions corresponding to the positions of the subsegments, respectively, and pipe adapters 142D1, 142D2, and 142D3 are mounted to those working holes, respectively. The dispersing mechanisms 3C are provided to the 41st subsegment RD1, the 42nd subsegment RD2, and the 43rd subsegment RD3, respectively. The segments other than the fourth segment RD may be sub-partitioned in a similar manner.

Figure 20A:
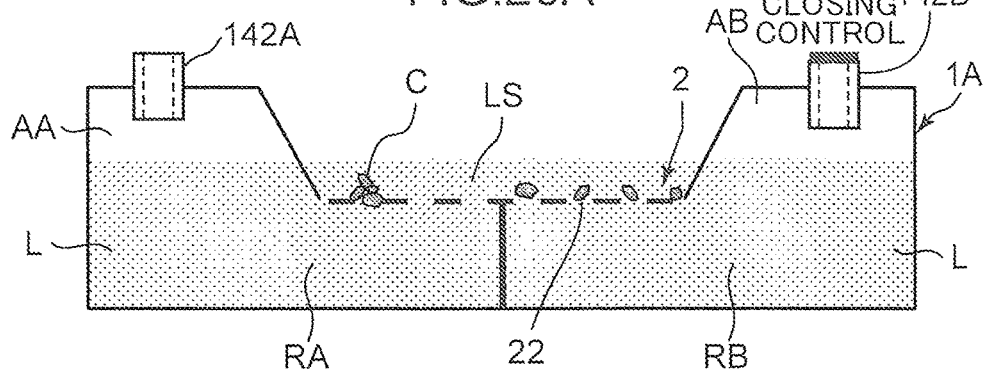
FIG. 20A is a view illustrating a situation in which cell aggregates are charged into the container in the holding device of the third embodiment.

With the holding device D3 having the configuration described above, the dispersing operation for the cell aggregates C can be performed for each of the first, second, third, and fourth segments RA, RB, RC, and RD. An example of such a partial dispersing operation is described with reference to FIG. 20A to FIG. 20C. FIG. 20A is a view illustrating a situation in which the cell aggregates C are charged into the container 1A from the upper opening 1H by the dispenser tip (not shown) in the holding device D3. When the cell aggregates C are to be charged, the controller 37 does not operate the first and second pumps 35A and 35B. Thus, neither of the pressurization force and the suction force acts on a space AA in the first segment RA and a space AB in the second segment RB in the closed region CA.

In this case, FIG. 20A exemplifies a situation in which the dispersing state of the cell aggregates C on the plate 2 is not satisfactory in the first segment RA but is satisfactory in the second segment RB. For example, when the dispersing state of the cell aggregates C is also satisfactory in the third and fourth segments RC and RD, the controller 37 determines that the dispersing operation is necessary only in the first segment RA. After the determination, the controller 37 causes the first valve device 36A to be "opened", and causes the second valve device 36B to be "closed" (the same applies to the valve devices in the third and fourth segments RC and RD). That is, the pressurization or depressurization is enabled for the space AA in the first segment RA, and the space AB in the second segment RB is shut off from outside air.

Figure 20B:
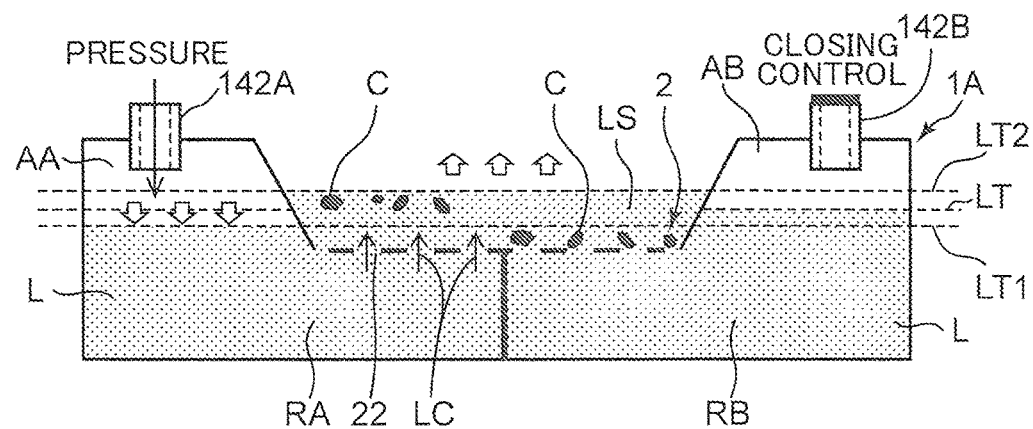
FIG. 20B is a view illustrating a situation in which liquid flows are generated in one segment through pressure application so that the cell aggregates are stirred up.

FIG. 20B is a view illustrating a situation in which a pressure is applied to the space AA in the first segment RA. In order to apply the pressure, the controller 37 operates the first pump 35A in the discharge mode to send a predetermined amount of air into the space AA through the pipe adapter 142A. Through this sending of the air, the inside of the space AA is pressurized, and hence the level of the liquid surface LT in the closed region CA in the first segment RA is decreased to the lower level LT1. The pressure of the liquid L that has received the pressure is released to the through holes 22 of the plate 2 which belong to the first segment RA. Therefore, the liquid flows LC, which flow from the lower side to the upper side, are generated in the through holes 22 in the first segment RA.

Along with the generation of the liquid flows LC, a part of the liquid L in the first segment RA flows toward the upper surface side of the plate 2. Thus, the liquid surface LT in the upper liquid layer LS above the plate 2 is raised to the upper level LT2. Further, the liquid flows LC cause the cell aggregates C carried on the plate 2 in the region belonging to the first segment RA to be stirred upward in the upper liquid layer LS at the upper level LT2. Thus, the cell aggregates C in a concentrated state are dispersed.

On the other hand, the liquid flows LC are not generated in the second segment RB. Further, even if the pressure is increased as the liquid surface in the upper liquid layer LS is raised, the volume of the space AB is not changed because the pipe adapter 142B in the second segment RB is closed. That is, the level of the liquid surface LT in the closed region CA in the second segment RB is not changed. Thus, the cell aggregates C carried on the plate 2 in the region belonging to the second segment RB are not moved.

After that, the controller 37 stops the first pump 35A to cancel the pressurized state in the space AA. Thus, the space AA gradually recovers the outside air pressure. The liquid surface LT at the upper level LT2 in the upper liquid layer LS is lowered, and the liquid surface LT at the lower level LT1 in the first segment RA is raised. Then, as in the state of FIG. 20A, the liquid surface LT has a constant level over the entire container 1A. Then, the stirred-up cell aggregates C in the first segment RA precipitate due to the self-weight, and are then carried on the plate 2 (holding portions 21).

Figure 20C:
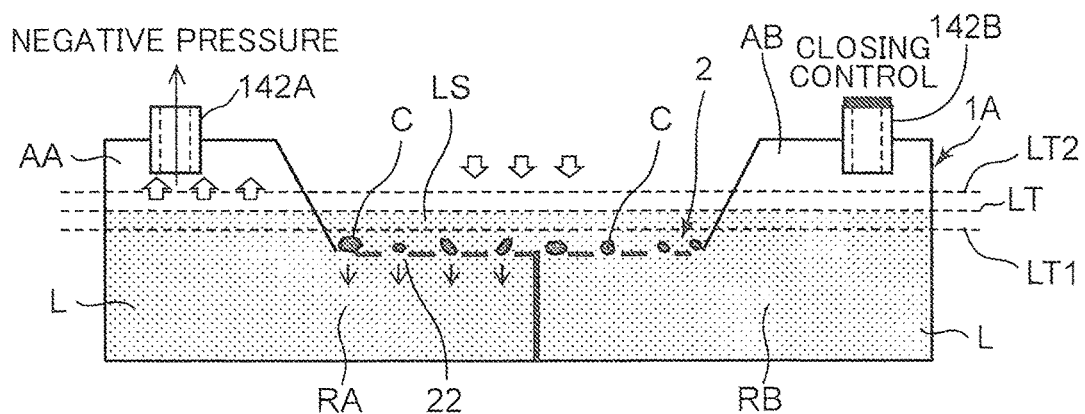
FIG. 20C is a view illustrating a situation in which the cell aggregates in the one segment precipitate on the plate while being assisted by a negative pressure.

Note that, when the rate of natural precipitation of the cell aggregates C is low, it is desired that the space AA be set to have a negative pressure as described above with reference to FIG. 12C. FIG. 20C illustrates a situation in which the precipitation of the cell aggregates C on the plate 2 in the first segment RA is promoted while being assisted by a negative pressure. This situation is a situation in which the controller 37 operates the pump 35A in the suction mode so that the air in the space AA is sucked through the pipe adapter 142A and therefore the space AA is depressurized. Thus, the precipitation of the cell aggregates C can be promoted.

In the above, a case where the dispersion of the cell aggregates C is necessary only in the first segment RA is exemplified. When the dispersion of the cell aggregates C is necessary in all of the first, second, third, and fourth segments RA, RB, RC, and RD, it is only necessary that the valve devices connected to the pipe adapters of all the segments are "opened" and the dispersing operation for the first segment RA that is described above is executed in all the segments.

Description of Pipe Examples

Figure 21:
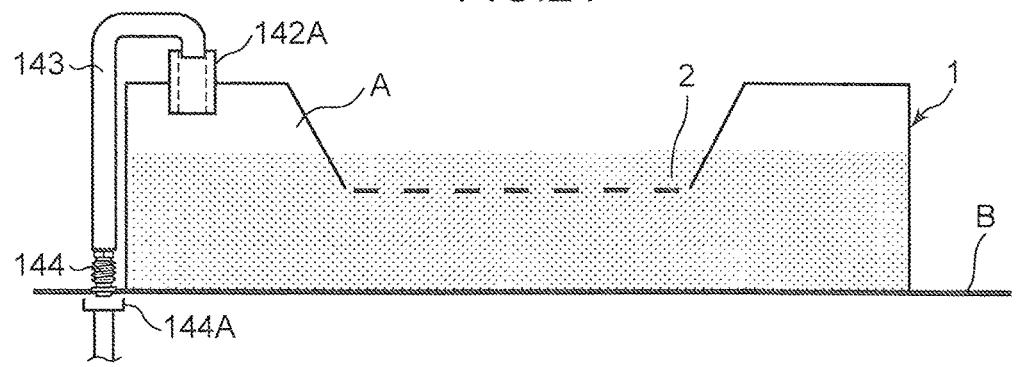
FIG. 21 is a view illustrating an example of a pipe to be laid on the container.

Preferred examples of the pipe for the container 1 are now described with reference to FIG. 21 to FIG. 23. What is given herein is the forms of pipes provided as substitutes for the air pipe 311 in the embodiment using an air pressure, which is exemplified as the first embodiment. FIG. 21 illustrates a pipe example including an elbow pipe 143 and a one-touch joint 144. One end of the elbow pipe 143 is connected to the pipe adapter 142A of the container 1, and the one-touch joint 144 is mounted to the other end of the elbow pipe 143. The container 1 is placed on a table B. An air suction/discharge pipeline similar to the air pipe 311 with the pump 31 as illustrated in FIG. 11 is provided to the table B. A receptacle 144A, which is a terminal end portion of the suction/discharge pipeline and is configured to receive the one-touch joint 144, is provided on an upper surface of the table B. In this pipe example, there is an advantage in that an air suction/discharge path for the space A can be secured only by placing the container 1 on the table B and connecting the one-touch joint 144 to the receptacle 144A.

Figure 22:
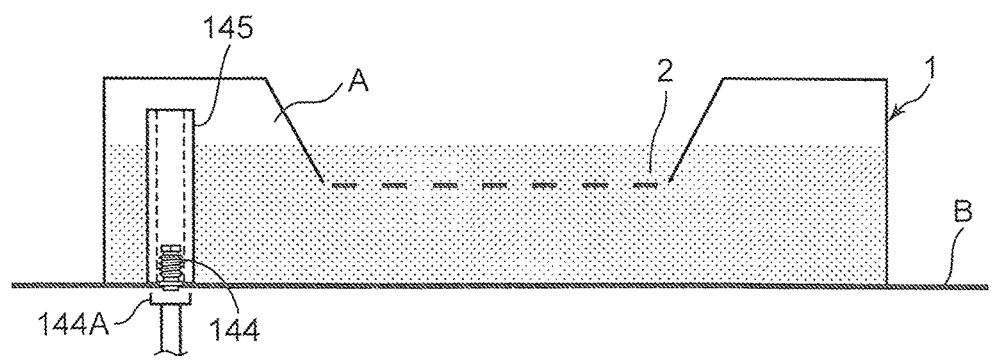
FIG. 22 is a view illustrating another example of the pipe to be laid on the container.

A pipe example of FIG. 22 includes the one-touch joint 144, and an internal pipe 145 arranged in the container 1. The internal pipe 145 is a straight pipe having a length larger than the height of the liquid surface of the liquid stored in the container 1. The upper end of the internal pipe 145 is opened in the space A, and the one-touch joint 144 is mounted to the lower end of the internal pipe 145. A joint part of the one-touch joint 144 protrudes downward from the bottom wall of the container 1. The receptacle 144A similar to that of the pipe example of FIG. 21 is provided on the table B. In this pipe example, the air suction/discharge path for the space A can be secured only by placing the container 1 on the table B in a state in which the one-touch joint 144 is positioned with respect to the receptacle 144A.

Figure 23:
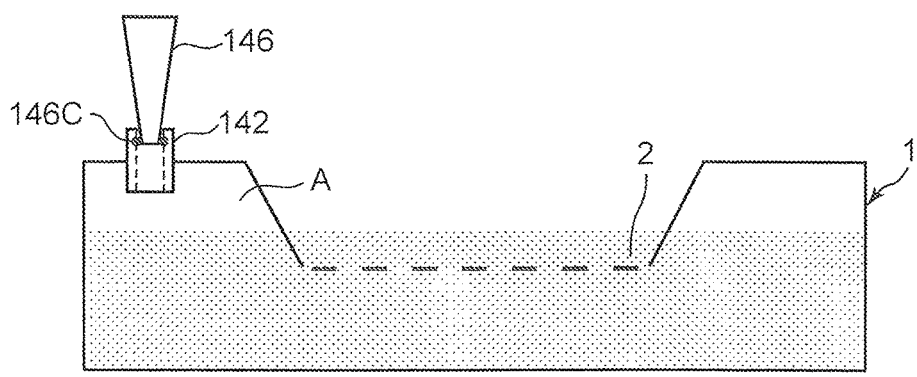
FIG. 23 is a view illustrating another example of the pressure application to the container.

A pipe example of FIG. 23 is a pipe example in which the distal end of a pipette tip 146 is fitted into the pipe adapter 142. A seal ring 146C for securing sealability is attached to an inner peripheral surface of the pipe adapter 142. The pipette tip 146 is capable of performing air suction/discharge through a distal end opening. Examples of the pipette tip 146 to be used may include a pipette tip configured to perform the suction/discharge through a mechanical operation of a piston member, and a pipette tip configured to perform the suction/discharge through a manual operation. Alternatively, the dispenser tip 4 that sucks no liquid may be used as a substitute for the pipette tip 146. The operation of the pipette tip 146 enables the air discharge and suction for the space A.

The object-holding device in the embodiments as described above can hold objects (cell aggregates C) in a satisfactorily dispersed state on the plate 2 including the plurality of holding portions 21 configured to carry the objects. Thus, observation of the objects on the plate 2, work of picking up the objects from the plate 2, and the like can be performed satisfactorily.

Note that the specific embodiments described above mainly include the disclosure having the following configurations.

An object-holding device according to one aspect of the present disclosure includes: a container configured to store a liquid and including an upper opening for charging an object into the stored liquid, and a bottom wall; a plate having an upper surface and a lower surface and immersed into the liquid in a state in which the lower surface is spaced away from the bottom wall of the container, with this plate including: one or a plurality of holding portions arranged on the upper surface side and configured to carry the object; and a through hole formed at a position, at which the holding portion is arranged, and passing through the holding portion from the upper surface to the lower surface; and a dispersing mechanism configured to form, in the through hole, a liquid flow which flows from the lower surface side toward the upper surface side to raise the object carried on the holding portion.

According to the holding device, each of the holding portions has the through hole. The dispersing mechanism generates, in the through hole, the liquid flow, which flows from the lower surface side toward the upper surface side. The liquid flow raises the object carried on the holding portion. Therefore, the object temporarily carried on the holding portion can be stirred up by the liquid flow. For example, even if a plurality of objects are carried on one holding portion, some or all of the objects can be stirred up by the liquid flow and moved to other holding portions. Thus, a large number of objects charged into the container can be carried satisfactorily dispersively on the respective holding portions on the upper surface of the plate. Alternatively, the orientation of the object carried on the holding portion can be changed by the liquid flow so that the observability of the object can be obtained satisfactorily.

In the object-holding device, it is desired that: the holding portion be a recess opened upward; and an opening of the through hole on the upper surface side be arranged on a bottom surface of the recess.

According to the holding device, the holding portion is formed from the recess, and hence the object can satisfactorily be held in a state in which the object is secured by the side wall surface of the recess. On the other hand, the opening of the through hole is arranged on the bottom surface of the recess, and hence the object located in the recess can easily be stirred up and dispersed by the liquid flow.

In the object-holding device, it is desired that: the container include: a tubular inner peripheral wall including: an upper end portion configured to define the upper opening, and a lower end portion configured to hold a peripheral edge of the plate; and a tubular outer peripheral wall including an upper edge portion continuously provided to the inner peripheral wall and a lower edge portion continuously provided to the bottom wall; the inner peripheral wall, the outer peripheral wall, the bottom wall, and the plate form a closed region, and in a state in which the container stores the liquid so that a liquid surface of the liquid is positioned above the plate, the through hole be closed by the liquid retained on the plate such that the closed region becomes a sealed region; and the dispersing mechanism form the liquid flow by generating a pressurization force in the closed region.

According to the holding device, the closed region is formed by the features of the container and the plate in terms of the shapes. The liquid flow is formed by generating the pressurization force in the closed region. Thus, the liquid flow can be generated with a simple mechanism.

In this case, in the object-holding device, it is desired that: the closed region is formed with a space in which air is retained; and the dispersing mechanism include a pressure regulator configured to pressurize the space. According to the holding device, the liquid flow can be generated by using an air pressure.

Further, it is desired that the pressure regulator further have a function of depressurizing the space, and perform the depressurization after the pressurization.

According to the holding device, after the object is stirred up by the liquid flow, the rate of precipitation of the object toward the plate in the liquid can be increased through the depressurization. Thus, the working time required to disperse the object can be shortened.

In the object-holding device, it is desired that the dispersing mechanism include a bulging member capable of changing a state thereof between a bulging state, in which the bulging member bulges in the liquid which is present in the closed region, and a retreating state, in which the bulging no longer exists. According to the holding device, the liquid flow can be generated on the basis of the bulging operation of the bulging member in the liquid.

It is desired that: the object-holding device further include a partition wall configured to partition the closed region into a plurality of segments; and the dispersing mechanism be provided for each of the segments of the closed region.

According to the holding device, the object can be carried onto the holding portion and dispersed by the liquid flow for each of the regions partitioned by the partition wall. Thus, for example, such an operation can be achieved that the dispersing operation is performed in a region in which the dispersing state of the object is not satisfactory and the dispersing operation is not performed in a region in which the dispersing state of the object is satisfactory.

In the object-holding device, it is desired that the object be a biological cell, in particular, a cell aggregate.

The object-holding device according to the present disclosure described above can hold the object in a satisfactorily dispersed state on the plate including the plurality of holding portions configured to carry the object. Thus, a holding device suitable for execution of sorting, observation, cultivation, and the like of the object can be provided.

The invention claimed is:

1. An object-holding device, comprising:
   a container configured to store a liquid and having an upper opening for charging an object into the stored liquid, and a bottom wall;
   a plate having an upper surface and a lower surface and immersed into the liquid in a state in which the lower surface is spaced away from the bottom wall of the container, the plate including one or a plurality of holding portions arranged on the upper surface side and configured to carry the object, and a through hole formed at a position at which, the holding portion is arranged, and passing through the holding portion from the upper surface to the lower surface; and
   a dispersing mechanism configured to form, in the through hole, a liquid flow which flows from the lower surface side toward the upper surface side to raise the object carried on the holding portion, wherein
   the container includes:
      a tubular inner peripheral wall including an upper end portion configured to define the upper opening, and a lower end portion configured to hold a peripheral edge of the plate;
      a tubular outer peripheral wall including an upper edge portion continuously provided to the inner peripheral wall and a lower edge portion continuously provided to the bottom wall; and
      a closed region that the inner peripheral wall, the outer peripheral wall, the bottom wall, and the plate form, and in a state in which the container stores the liquid so that a liquid surface of the liquid is positioned above the plate, the through hole is closed by the liquid retained on the plate such that the closed region becomes a sealed region; and
   wherein
   the dispersing mechanism forms the liquid flow by generating a pressurization force to the liquid surface in the closed region,
   the closed region is formed with a space in which air is retained, and
   the dispersing mechanism includes a pressure regulator configured to pressurize the space.

2. The object-holding device according to claim 1, wherein
   the holding portion is a recess opened upward; and
   an opening of the through hole on the upper surface side is arranged on a bottom surface of the recess.

3. The object-holding device according to claim 1, wherein the pressure regulator further has a function of depressurizing the space, and performs the depressurization after the pressurization.

4. The object-holding device according to claim 1, wherein the dispersing mechanism includes a bulging member capable of changing a state thereof between a bulging state, in which the bulging member bulges in the liquid which is present in the closed region and a retreating state, in which the bulging no longer exists.

5. The object-holding device according to claim 1, further comprising a partition wall configured to partition the closed region into a plurality of segments, wherein
   the dispersing mechanism is provided for each of the segments of the closed region.

6. The object-holding device according to claim 1, wherein the object is a biological cell.

* * * * *